United States Patent [19]

Mausner

[11] Patent Number: 5,571,503

[45] Date of Patent: Nov. 5, 1996

[54] ANTI-POLLUTION COSMETIC COMPOSITION

[76] Inventor: Jack Mausner, 150 E. 69th St., New York, N.Y. 10021

[21] Appl. No.: 510,077

[22] Filed: Aug. 1, 1995

[51] Int. Cl.$^6$ .................. A61K 7/42; A61K 7/00
[52] U.S. Cl. .................. 424/59; 424/195.1; 424/401
[58] Field of Search .................. 424/59, 195.1, 424/401

[56] References Cited

U.S. PATENT DOCUMENTS

| | | | |
|---|---|---|---|
| 3,697,643 | 10/1972 | Shepherd et al. | 424/63 |
| 3,864,275 | 2/1975 | Kan et al. | 252/316 |
| 3,911,105 | 10/1975 | Papantoniou et al. | 424/64 |
| 3,966,398 | 6/1976 | Vanlerberghe et al. | 8/11 |
| 4,125,549 | 11/1978 | Coopersmith et al. | 424/64 |
| 4,247,411 | 1/1981 | Vanlerberghe et al. | 252/316 |
| 4,369,037 | 1/1983 | Matsunaga et al. | 8/127.51 |
| 4,400,295 | 8/1983 | Ootsu et al. | 252/356 |
| 4,423,031 | 12/1983 | Murui et al. | 424/63 |
| 4,460,371 | 7/1984 | Abber | 604/897 |
| 4,481,186 | 11/1984 | Deckner | 424/59 |
| 4,549,990 | 10/1985 | Seguin et al. | 260/397.25 |
| 4,574,082 | 3/1986 | Tietjen et al. | 424/63 |
| 4,608,392 | 8/1986 | Jacquet et al. | 514/844 |
| 4,752,496 | 6/1988 | Fellows et al. | 427/27 |
| 4,758,599 | 7/1988 | Minetti | 514/844 |
| 4,820,510 | 4/1989 | Arraudeau et al. | 424/63 |
| 4,855,131 | 8/1989 | Iris | 514/844 |
| 4,880,621 | 11/1989 | Grollier et al. | 424/74 |
| 4,883,659 | 11/1989 | Goodman et al. | 424/78 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/2 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne et al. | 514/2 |
| 5,043,323 | 8/1991 | Bombardelli et al. | 514/25 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |
| 5,064,675 | 11/1991 | Jensen | 424/597 |
| 5,093,109 | 3/1992 | Mausner | 424/63 |
| 5,116,607 | 5/1992 | Jones | 424/70 |
| 5,182,103 | 1/1993 | Nakane et al. | 424/78.03 |
| 5,215,759 | 6/1993 | Mausner | 424/489 |
| 5,240,732 | 8/1993 | Ueda | 426/597 |
| 5,254,331 | 10/1993 | Mausner | 424/59 |
| 5,352,441 | 10/1994 | Mausner | 424/64 |
| 5,391,373 | 2/1995 | Mausner | 424/401 |
| 5,415,875 | 5/1995 | Kaoki et al. | 424/581 |

*Primary Examiner*—Sallie M. Gardner
*Attorney, Agent, or Firm*—Merchant, Gould, Smith, Edell, Welter & Schmidt

[57] ABSTRACT

A cosmetic composition according to the present invention incorporates a new combination of ingredients particularly designed to provide significant protection of the skin from several damaging components of environmental pollution, while also providing significant protection against moisture loss and damage due to free radical activity and ultraviolet light, both UV-A and UV-B, and controlling oil. In general, a cosmetic composition according to the present invention comprises: water, and emulsified and dispersed in the water: (1) an anti-pollution complex comprising propylene glycol, hydrolyzed wheat protein, mannitol, glycogen, yeast extract, ginseng extract, linden extract, calcium pantothenate, horse chestnut extract, and biotin; (2) a micellar complex comprising: phospholipids, glycosphingolipids, panthenol, Crataegus extract, cholesterol, and sodium hyaluronate; (3) an anti-free radical complex comprising melanin, a short-chain fatty acid ester of tocopherol, a long-chain fatty acid ester of retinol, and a long-chain fatty acid ester of ascorbic acid; and (4) a sunscreen. Other cosmetic components, such as aloe extract, matricaria extract, apricot kernel extract, garden balsam leaf extract, hydrolyzed soy protein, and horsetail extract, and ancillary components can also be used.

62 Claims, No Drawings

ANTI-POLLUTION COSMETIC COMPOSITION

BACKGROUND

This application is directed to an improved anti-pollution cosmetic composition.

Modern environmental conditions, such as heating and air conditioning, dryness, exposure to the sun, and environmental pollution, exert severe stress on the skin and accelerate the natural aging process, resulting in wrinkles, loss of firmness and elasticity, age spots, discoloration, dryness, and other cosmetically undesirable effects. Among the most damaging pollutants are hydrogen chloride, formaldehyde, chloroform, sulfur dioxide, carbon monoxide, tobacco smoke, car exhaust fumes, and nitrogen dioxide. Among the other environmental effects that can damage skin are oxygen deprivation (anoxia) and formation of free radicals.

Although a number of cosmetic compositions for use on the skin or over the eyes already exist, there is a need for a simple-to-apply and effective all-in-one cosmetic treatment, such as a cosmetic composition that can be formulated for use on the skin or over the eyes, that can simultaneously: (1) reduce the damaging effect of exposure to the sun; (2) reduce damage due to free radicals; (3) reduce moisture loss; and (4) very importantly, protect the skin against the most damaging environmental pollutants. Additionally, there is a need for a cosmetic composition that can provide these advantages while reducing the amount of oil and sebum on the skin of people with oily skin.

SUMMARY

I have developed a cosmetic composition incorporating a new combination of ingredients particularly designed to provide protection from environmental pollution, in addition to protection from ultraviolet light, protection from free radical activity, and moisturization of the skin. The cosmetic composition of the present invention, in particular, provides protection against many of the most damaging pollutants while providing, simultaneously, moisturization and control of oil, where necessary.

In general, a cosmetic composition according to the present invention comprises: water, and emulsified and dispersed in the water:

(1) an anti-pollution complex comprising propylene glycol, hydrolyzed wheat protein, mannitol, glycogen, yeast extract, ginseng extract, linden extract, calcium pantothenate, horse chestnut extract, and biotin;

(2) a micellar complex comprising: phospholipids, glycosphingolipids, panthenol, cholesterol, Crataegus extract, and sodium hyaluronate;

(3) an anti-free radical complex comprising melanin, a short-chain fatty acid ester of tocopherol, a long-chain fatty acid ester of retinol, and a long-chain fatty acid ester of ascorbic acid; and (4) a sunscreen.

The anti-pollution complex, the micellar complex, and the anti-free radical complex each is present in a quantity sufficient to detectably reduce the damaging effect of at least one environmental stress selected from the group consisting of environmental pollutants, moisture loss, and free radical activity on the skin of a wearer to whom the composition is applied. The sunscreen is present in a quantity sufficient to protect the skin against at least one of UV-A and UV-B solar radiation.

The micellar complex can further include sodium pyrrolidone carboxylic acid. Alternatively, the micellar complex can further include from one to two components selected from the group consisting of cholesteryl/behenyl/octyldodecyl lauroyl glutamate and lysine lauroyl methionate.

In some embodiments, particularly for cosmetic compositions intended for application to the skin, the sunscreen comprises an anti-actinic complex comprising oxybenzone and a medium-chain methoxycinnamate ester selected from the group consisting of octyl methoxycinnamate, heptyl methoxycinnamate, nonyl methoxycinnamate, and mixtures thereof. Preferably, the medium-chain methoxycinnamate ester is octyl methoxycinnamate. Alternatively, the sunscreen can comprise titanium dioxide.

Other cosmetic components can also be included, such as aloe extract, matricaria extract, apricot kernel extract, garden balsam leaf extract, hydrolyzed soy protein, and horsetail extract. These can be included in various combinations, including: (1) aloe extract, matricaria extract, apricot kernel extract, and garden balsam leaf extract; (2) aloe extract, matricaria extract, apricot kernel extract, and hydrolyzed soy protein; and (3) aloe extract, matricaria extract, and apricot kernel extract.

The retinol ester can be selected from the group consisting of retinyl palmitate, retinyl myristate, and retinyl stearate. Preferably, the retinol ester is retinyl palmitate.

The ascorbic acid ester can be selected from the group consisting of ascorbyl palmitate, ascorbyl myristate, and ascorbyl stearate. Preferably, the ascorbic acid ester is ascorbyl palmitate.

The tocopherol ester can be selected from the group consisting of tocopheryl acetate and tocopheryl propionate. Preferably, the tocopherol ester is tocopheryl acetate.

In addition to the cosmetic components, cosmetic compositions according to the present invention can also comprise additional, ancillary ingredients whose use is optional but preferable. These ancillary ingredients can include: (1) a solvent component; (2) a preservative component; (3) a thickener component; (4) a hydrophilic component; (5) a lipid-soluble component; and (6) pigment.

The solvent component can comprise from one to two ingredients, each ingredient being selected from the group consisting of butylene glycol and hexylene glycol.

The lipid-soluble component can comprise from 1 to 20 ingredients, each ingredient being selected from the group consisting of (1) neopentyl glycol dioctanoate diisostearate; (2) a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof; (3) cetearyl glucoside; (4) squalane; (5) dimethicone; (6) mineral oil; (7) cetyl alcohol; (8) steareth-2; (9) steareth-21; (10) laureth-7; (11) PEG-40 hydrogenated castor oil; (12) $C_{13}$–$C_{14}$ isoparaffin; (13) a medium-chain carboxylic acid ester of cetyl alcohol selected from the group consisting of cetyl octanoate, cetyl heptanoate, cetyl nonanoate, and mixtures thereof; (14) isodecyl oleate; (15) dicaprylyl maleate; (16) octyldodecyl neopentanoate; (17) a long-chain fatty acid ester of glycerol selected from the group consisting of glyceryl stearate, glyceryl palmitate, glyceryl arachidate, and mixtures thereof; (18) PEG-100 stearate; (19) caprylic/capric triglyceride; and (20) simethicone. Various combinations of these ingredients can be used in the lipid-soluble component.

The thickener component can comprise from one to four ingredients, each ingredient being selected from the group consisting of polyacrylamide, carrageenan, xanthan gum, and silica. Various combinations of these ingredients can be used in the thickener component.

A preferred pigment is titanium dioxide.

The hydrophilic component can comprise from 1 to 10 ingredients, each ingredient being selected from the group consisting of fructose, glucose, sucrose, urea, dextrin, alanine, glutamic acid, glycerin, aspartic acid, and hexyl nicotinate. Various combinations of these ingredients can be used in the hydrophilic component.

The preservative component can comprise from 1 to 7 ingredients, each ingredient being selected from the group consisting of sodium citrate, a sodium salt of EDTA selected from the group consisting of disodium EDTA and trisodium EDTA, phenoxyethanol, chlorphenesin, methylparaben, propylparaben, and butylparaben. Various combinations of these ingredients can be used in the preservative component.

One particularly preferred cosmetic composition according to the present invention comprises: water and emulsified and dispersed in the water:

(1) about 0.01% to about 2.0% of propylene glycol;

(2) about 0.01% to about 1.0% of hydrolyzed wheat protein;

(3) about 0.001% to about 1.0% of mannitol;

(4) about 0.001% to about 1.0% of glycogen;

(5) about 0.001% to about 1.0% of yeast extract;

(6) about 0.001% to about 1.0% of ginseng extract;

(7) about 0.001% to about 1.0% of linden extract;

(8) about 0.001% to about 1.0% of calcium pantothenate;

(9) about 0.001% to about 1.0% of horse chestnut extract;

(10) about 0.001% to about 1.0% of biotin;

(11) about 0.001% to about 1.0% of phospholipids;

(12) about 0.001% to about 1.0% of glycosphingolipids;

(13) about 0.001% to about 1.0% of Crataegus extract;

(14) about 0.01% to about 2.0% of panthenol;

(15) about 0.01% to about 2.0% of sodium hyaluronate;

(16) about 0.1% to about 2.0% of sodium pyrrolidone carboxylic acid;

(17) about 0.001% to about 1.0% of cholesterol;

(18) about 0.001% to about 1.0% of cholesteryle/behenyl/octyldodecyl lauroyl glutamate;

(19) about 0.001% to about 1.0% of lysine lauroyl methionate;

(20) about 0.001% to about 1.0% of melanin;

(21) about 0.01% to about 2.0% of tocopheryl acetate;

(22) about 0.01% to about 2.0% of retinyl palmitate;

(23) about 0.01% to about 2.0% of ascorbyl palmitate;

(24) about 0.01% to about 2.0% of aloe extract;

(25) about 0.01% to about 2.0% of matricaria extract;

(26) about 0.001% to about 1.0% of apricot kernel extract;

(27) about 0.01% to about 2.0% of garden balsam leaf extract;

(28) about 2.0% to about 7.5% of octyl methoxycinnamate;

(29) about 2.0% to about 6.0% of oxybenzone;

(30) about 2.0 % to about 5.0% of neopentyl glycol dioctanoate diisostearate;

(31) about 2.0% to about 5.0% of octyl palmitate;

(32) about 1.0% to about 4.0% of cetearyl glucoside;

(33) about 1.0 % to about 3.0% of squalane;

(34) about 1.0 % to about 3.0% of dimethicone;

(35) about 0.01% to about 2.0% of mineral oil;

(36) about 0.1% to about 2.0% of cetyl alcohol;

(37) about 0.1% to about 2.0% of steareth-2;

(38) about 0.1% to about 3.0% of steareth-21;

(39) about 0.1% to about 2.0% of laureth-7;

(40) about 0.1% to about 2.0% of PEG-40 hydrogenated castor oil;

(41) about 0.1% to about 2.0% of $C_{13}$–$C_{14}$ isoparaffin;

(42) about 0.1% to about 2.0% of polyacrylamide;

(43) about 0.01% to about 2.0% of butylene glycol;

(44) about 0.01% to about 1.0% of sodium citrate;

(45) about 0.01% to about 1.0% of disodium EDTA;

(46) about 0.01% to about 1.0% of chlorphenesin;

(47) about 0.01% to about 1.0% of methylparaben;

(48) about 0.01% to about 1.0% of propylparaben;

(49) about 0.01% to about 1.0% of butylparaben; and

(50) about 0.01% to about 1.0% of phenoxyethanol.

In this composition, the propylene glycol, the hydrolyzed wheat protein, the mannitol, the glycogen, the yeast extract, the ginseng extract, the linden extract, the calcium pantothenate, the horse chestnut extract, and the biotin comprise an anti-pollution complex. The phospholipids, the glycosphingolipids, the Crataegus extract, the sodium hyaluronate, the sodium pyrrolidone carboxylic acid, the panthenol, the cholesterol, the cholesteryl/behenyl/octyldodecyl lauroyl glutamate, and the lysine lauroyl methionate comprise a micellar complex. The octyl methoxycinnamate and the oxybenzone comprise an anti-actinic complex. The melanin, the tocopheryl acetate, the retinyl palmitate, and the ascorbyl palmitate comprise an anti-free radical complex.

A second particularly preferred cosmetic composition according to the present invention comprises: water and emulsified and dispersed in the water:

(1) about 0.01% to about 2.0% of propylene glycol;

(2) about 0.01% to about 2.0% of hydrolyzed wheat protein;

(3) about 0.001% to about 1.0% of mannitol;

(4) about 0.001% to about 1.0% of glycogen;

(5) about 0.001% to about 1.0% of yeast extract;

(6) about 0.001% to about 1.0% of ginseng extract;

(7) about 0.001% to about 1.0% of linden extract;

(8) about 0.001% to about 1.0% of calcium pantothenate;

(9) about 0.001% to about 1.0% of horse chestnut extract;

(10) about 0.001% to about 1.0% of biotin;

(11) about 0.001% to about 1.0% of phospholipids;

(12) about 0.001% to about 1.0% of glycosphingolipids;

(13) about 0.01% to about 2.0% of panthenol;

(14) about 0.001% to about 1.0% of Crataegus extract;

(15) about 0.001% to about 1.0% of cholesterol;

(16) about 2.0% to about 7.5% of octyl methoxycinnamate;

(17) about 2.0% to about 6.0% of oxybenzone;

(18) about 0.001% to about 1.0% of melanin;

(19) about 0.01% to about 2.0% of tocopheryl acetate;

(20) about 0.01% to about 2.0% of retinyl palmitate;

(21) about 0.01% to about 2.0% of ascorbyl palmitate;

(22) about 0.01% to about 2.0% of aloe extract;

(23) about 0.01% to about 2.0% of matricaria extract;

(24) about 0.001% to about 1.0% of apricot kernel extract;

(25) about 0.01% to about 1.0% of hydrolyzed soy protein;

(26) about 1.0% to about 5.0% of cetyl octanoate;

(27) about 1.0% to about 5.0% of isodecyl oleate;

(28) about 1.0% to about 5.0% of dicaprylyl maleate;

(29) about 1.0% to about 5.0% of octyldodecyl neopentanoate;

(30) about 0.1% to about 2.0% of glyceryl stearate;

(31) about 0.1% to about 2.0% of steareth-2;

(32) about 0.1% to about 3.0% of steareth-21;

(33) about 0.1% to about 2.0% of $C_{13}$–$C_{14}$ isoparaffin;

(34) about 0.1% to about 2.0% of PEG-100 stearate;

(35) about 0.1% to about 2.0% of cetyl alcohol;

(36) about 0.1% to about 2.0% of laureth-7;

(37) about 1.0% to about 3.0% of dimethicone;

(38) about 0.1% to about 2.0% of polyacrylamide;

(39) about 0.01% to about 2.0% of carrageenan;

(40) about 0.01% to about 1.0% of xanthan gum;

(41) about 0.1% to about 3.0% of silica;

(42) about 0.01% to about 2.0% of glycerin;

(43) about 0.1% to about 2.0% of butylene glycol;

(44) about 0.01% to about 1.0% of simethicone;

(45) about 0.1% to about 2.0% of PEG-40 hydrogenated castor oil;

(46) about 0.01% to about 2.0% of mineral oil;

(47) about 0.01% to about 1.0% of sodium citrate;

(48) about 0.01% to about 1.0% of trisodium EDTA;

(49) about 0.01% to about 1.0% of phenoxyethanol;

(50) about 0.01% to about 1.0% of chlorphenesin;

(51) about 0.01% to about 1.0% of methylparaben;

(52) about 0.01% to about 1.0% of butylparaben;

(53) about 0.01% to about 1.0% of propylparaben; and

(54) about 0.01% to about 1.0% of titanium dioxide.

In this composition, the propylene glycol, the hydrolyzed wheat protein, the mannitol, the glycogen, the yeast extract, the ginseng extract, the linden extract, the calcium pantothenate, the horse chestnut extract and the biotin comprise an anti-pollution complex. The phospholipids, the panthenol, the Crataegus extract, and the cholesterol comprise a micellar complex. The octyl methoxycinnamate and the oxybenzone comprise an anti-actinic complex. The melanin, the tocopheryl acetate, the retinyl palmitate, and the ascorbyl palmitate comprise an anti-free radical complex.

A third particularly preferred cosmetic composition according to the present invention comprises:

(1) about 0.01% to about 2.0% of propylene glycol;

(2) about 0.01% to about 1.0% of hydrolyzed wheat protein;

(3) about 0.001% to about 1.0% of mannitol;

(4) about 0.001% to about 1.0% of glycogen;

(5) about 0.001% to about 1.0% of yeast extract;

(6) about 0.001% to about 1.0% of ginseng extract;

(7) about 0.001% to about 1.0% of linden extract;

(8) about 0.001% to about 1.0% of calcium pantothenate;

(9) about 0.001% to about 1.0% of horse chestnut extract;

(10) about 0.001% to about 1.0% of biotin;

(11) about 0.001% to about 1.0% of phospholipids;

(12) about 0.001% to about 1.0% of glycosphingolipids;

(13) about 0.01% to about 2.0% of panthenol;

(14) about 0.001% to about 1.0% of Crataegus extract;

(15) about 0.001% to about 1.0% of cholesterol;

(16) about 0.001% to about 1.0% of cholesteryl/behenyl/octyldodecyl lauroyl glutamate;

(17) about 0.001% to about 1.0% of lysine lauroyl methionate;

(18) about 0.001% to about 1.0% of melanin;

(19) about 0.01% to about 2.0% of tocopheryl acetate;

(20) about 0.01% to about 2.0% of retinyl palmitate;

(21) about 0.01% to about 2.0% of ascorbyl palmitate;

(22) about 0.01% to about 2.0% of aloe extract;

(23) about 0.01% to about 2.0% of matricaria extract;

(24) about 0.01% to about 2.0% of horsetail extract;

(25) about 0.1% to about 10.0% of titanium dioxide;

(26) about 2.0% to about 8.0% of neopentyl glycol dioctanoate diisostearate;

(27) about 2.0% to about 8.0% of octyl palmitate;

(28) about 1.0% to about 4.0% of cetearyl glucoside;

(29) about 1.0% to about 3.0% of squalane;

(30) about 1.0% to about 3.0% of dimethicone;

(31) about 1.0% to about 8.0% of caprylic/capric triglyceride;

(32) about 0.01% to about 2.0% of mineral oil;

(33) about 0.01% to about 2.0% of cetyl alcohol;

(34) about 0.01% to about 2.0% of steareth-2;

(35) about 0.1% to about 3.0% of steareth-21;

(36) about 0.1% to about 2.0% of laureth-7;

(37) about 0.1% to about 2.0% of PEG-40 hydrogenated castor oil;

(38) about 0.1% to about 2.0% of polyacrylamide;

(39) about 0.1% to about 2.0% of butylene glycol;

(40) about 0.01% to about 1.0% of xanthan gum;

(41) about 0.1% to about 5.0% of hexylene glycol;

(42) about 0.01% to about 2.0% of fructose;

(43) about 0.01% to about 2.0% of glucose;

(44) about 0.01% to about 2.0% of sucrose;

(45) about 0.01% to about 2.0% of urea;

(46) about 0.01% to about 2.0% of dextrin;

(47) about 0.01% to about 2.0% of alanine;

(48) about 0.01% to about 2.0% of glutamic acid;

(49) about 0.01% to about 2.0% of aspartic acid;

(50) about 0.01% to about 2.0% of hexyl nicotinate;

(51) about 0.1% to about 2.0% of $C_{13}$–$C_{14}$ isoparaffin;

(52) about 0.1% to about 2.0% of glycerin;

(53) about 0.01% to about 1.0% of sodium citrate;

(54) about 0.01% to about 1.0% of disodium EDTA;

(55) about 0.01% to about 1.0% of chlorphenesin;

(56) about 0.01% to about 1.0% of methylparaben;

(57) about 0.01% to about 1.0% of propylparaben;

(58) about 0.01% to about 1.0% of butylparaben; and

(59) about 0.01% to about 1.0% of phenoxyethanol.

In this composition, the propylene glycol, the hydrolyzed wheat protein, the mannitol, the glycogen, the yeast extract, the ginseng extract, the linden extract, the calcium pantothenate, the horse chestnut extract, and the biotin comprise an anti-pollution complex. The phospholipids, the glycosphingolipids, the panthenol, the Crataegus extract, the cholesterol, the cholesteryl/behenyl/octyldodecyl lauroyl glutamate, and the lysine lauroyl methionate comprise a micellar complex. The melanin, the tocopheryl acetate, the retinyl palmitate, and the ascorbyl palmitate comprise an anti-free radical complex.

DESCRIPTION

A new combination of ingredients results in a cosmetic composition that provides protection against many of the most damaging environmental pollutants, including chloroform, hydrogen chloride, formaldehyde, sulfur dioxide, carbon monoxide, tobacco smoke, car exhaust fumes, and nitrogen dioxide, as well as against other environmental stresses such as oxygen deprivation, free radicals, moisture loss, and exposure to the sun.

The cosmetic composition of the present invention comprises an aqueous base in which cosmetic components are emulsified and dispersed. The cosmetic components include: (1) an anti-pollution complex; (2) a micellar complex; (3) an anti-free radical complex; (4) a sunscreen; (5) optionally, hydrolyzed soy protein; (6) optionally, aloe extract; (7) optionally, matricaria extract; (8) optionally, apricot kernel extract; (9) optionally, garden balsam leaf extract; and (10) optionally, horsetail extract.

Typically, the composition of the present invention also comprises ancillary components such as: (1) a solvent component; (2) a preservative component; (3) a thickener component; (4) a hydrophilic component; (5) a lipid-soluble component; and (6) pigment.

The ingredients included within these components are described in detail below.

The ingredients are dispersed in an emulsified composition by the method of preparation described below. "Dispersed" refers to any process by which the ingredients are uniformly distributed in the emulsified base, and includes dissolving, emulsifying, and forming a colloidal suspension.

I. NATURE AND PROPORTION OF INGREDIENTS OF THE COSMETIC COMPOSITION

A. The Cosmetic Components

Each of the cosmetic components disclosed above contributes to the improved properties of the cosmetic composition of the present invention and is present in a quantity sufficient to detectably reduce the damaging effect of at least one environmental stress selected from the group consisting of environmental pollutants, moisture loss, and free radical activity on the skin of a wearer to whom the composition is applied. The term "environmental pollutants," as used herein, is defined as including at least one of the following pollutants: hydrogen chloride, formaldehyde, chloroform, anoxia (oxygen deprivation), sulfur dioxide, carbon monoxide, tobacco smoke, car exhaust fumes, and nitrogen dioxide. Cosmetic compositions according to the present invention can also protect against other environmental pollutants.

The optional cosmetic components provide additional beneficial effects.

Preferred compositions for these cosmetic components, including the optional cosmetic components, are now disclosed. However, other compositions containing the required ingredients set forth above are possible and are within the scope of the present invention.

1. The Anti-Pollution Complex

The anti-pollution complex comprises propylene glycol, hydrolyzed wheat protein, mannitol, glycogen, yeast extract, ginseng extract, linden extract, calcium pantothenate, horse chestnut extract, and biotin.

Typically, these ingredients are present in proportions in the cosmetic composition of the present invention such that the propylene glycol comprises from about 0.01% to about 2.0% of the composition, the hydrolyzed wheat protein comprises from about 0.01% to about 2.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, and the biotin comprises from about 0.001% to about 1.0% of the composition. In some cosmetic compositions according to the present invention, the hydrolyzed wheat protein typically comprises from about 0.01% to about 1.0% of the composition.

One source of the ingredients of the anti-pollution complex is a complex marketed as S.P.C. LS 8425 by Laboratoires Seroblologiques S.A., 3, rue de Seichamps, 55420 Pulnoy, France. Other commercially available sources of these ingredients exist.

2. The Micellar Complex

The micellar complex comprises phospholipids, glycosphingolipids, Crataegus (hawthorn blossom) extract, panthenol, and cholesterol. Optionally, the micellar complex can also comprise sodium hyaluronate, sodium pyrrolidone carboxylic acid, cholesteryl/behenyl/octyldodecyl lauroyl glutamate, and lysine lauroyl methionate.

In one particularly preferred embodiment, the micellar complex comprises phospholipids, glycosphingolipids, Crataegus extract, panthenol, cholesterol, sodium hyaluronate, sodium pyrrolidone carboxylic acid, cholesteryl/behenyl/octyldodecyl lauroyl glutamate, and lysine lauroyl methionate. In another particularly preferred embodiment, the micellar complex comprises phospholipids, glycosphingolipids, Crataegus extract, panthenol and cholesterol. In a third preferred alternative, the micellar complex comprises phospholipids, glycosphingolipids, Crataegus extract, panthenol, cholesterol, cholesteryl/behenyl/octyldodecyl lauroyl glutamate, and lysine lauroyl methionate.

In the first of these preferred alternatives, the concentrations of the components are such that the phospholipids comprise from 0.001% to about 1.0% of the composition, the glycosphingolipids comprise from about 0.001% to about 1.0% of the composition, the Crataegus extract comprises from about 0.001% to about 1.0% of the composition, the sodium hyaluronate comprises from about 0.01% to about 2.0% of the composition, the sodium pyrrolidone carboxylic acid comprises from about 0.1% to about 2.0% of the composition, the cholesterol comprises from about 0.001% to about 1.0% of the composition, the cholesteryl/behenyl/octyldodecyl lauroyl glutamate comprises from about 0.001% to about 1.0% of the composition, and lysine lauroyl methionate comprises from about 0.001% to about 1.0% of the composition.

In the second of these preferred alternatives, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the panthenol comprises from about 0.01% to about 2.0% of the composition, and the cholesterol comprises from about 0.001% to about 1.0% of the composition.

In the third of these preferred alternatives, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the panthenol comprises from about 0.01% to about 1.0% of the composition, the cholesterol comprises from about 0.01% to about 1.0% of the composition, the cholesteryl/behenyl/octyldodecyl lauroyl glutamate comprises from about 0.001% to about 1.0% of the composition, and the lysine lauroyl methionate comprises from about 0.001% to about 1.0% of the composition. These percentages, and other analogous percentages given below, refer to the proportion of the ingredient in the overall composition and not merely in the micellar complex.

The micellar complex provides significant hydration and moisturizing activities, as well as healing, soothing, calming, and anti-irritant activities. The micelles are colloidal vectors with an average particle size of less than 0.001 mm and are stable globular structures formed by lipids oriented such that their polar head groups are on the surface and their hydrocarbon tails are sequestered in the interior of the micelle. They are much smaller than any previously used "capsules" in cosmetics, e.g., liposomes, and can, therefore, penetrate the skin faster and to greater depth. There are also much more stable than liposomes and, therefore, are much more effective.

Crataegus extract is a plant extract that is believed to exert anti-stress, anti-inflammatory, calming, and soothing effects.

Panthenol is the racemic dl-form of 2,4-dihydroxy-N-(3-hydroxypropyl)-3,3-dimethylbutanamide, and is also known as vitamin $B_5$. It is believed to exert a calming, soothing, and protective effect on the skin.

The phospholipids can be phosphatidyl ethanolamine, phosphatidyl choline, phosphatidyl serine, phosphatidyl inositol, diphosphatidyl glycerol, and derivatives and/or mixtures thereof.

Glycosphingolipids comprise ceramide covalently bound to carbohydrate on the primary hydroxyl group of the ceramide. The carbohydrate is typically glucose, lactose, N-acetylglucosamine, N-acetylgalactosamine, or sialic acid. The glycosphingolipids are believed to have a powerful hydrating effect, together with the ability to restructure and reinforce the barrier effect to the skin and improve the cohesion of the corneocytes. They are also believed to have an overall soothing effect and to exert a protective role against environmental aggression.

3. The Sunscreen

The sunscreen can comprise either titanium dioxide or an anti-actinic complex. If an anti-actinic complex is used, titanium dioxide can optionally be used in addition; in that case, its primary function is that of a pigment. The sunscreen is present in a quantity sufficient to protect the skin against at least one of UV-A and UV-B solar radiation.

When the sunscreen is titanium dioxide, it is typically present in a concentration of from about 0.1% to about 10.0%.

When the anti-actinic complex is used, it provides a SPF of 15. Preferably, the anti-actinic complex comprises octyl methoxycinnamate and oxybenzone. Preferably, for compositions employing the anti-actinic complex, octyl methoxycinnamate comprises from about 2.0% to about 7.5% of the composition, and oxybenzone comprises from about 2.0% to about 6.0% of the composition.

4. The Anti-Free Radical Complex

The cosmetic composition of the present invention also includes an anti-free radical complex to protect the skin against free radicals. Typically, the anti-free radical complex comprises melanin, a long-chain fatty acid ester of retinol, a long-chain fatty acid ester of ascorbic acid, and a short-chain carboxylic acid ester of tocopherol.

In general, melanins are black or brown, insoluble, nitrogenous pigments produced by the oxidative polymerization of 5,6-dihydroxyindoles derived enzymatically from tyrosine via dopa (3-hydroxy-L-tyrosine).

Preferably, the long-chain fatty acid ester of retinol is selected from the group consisting of retinyl palmitate, retinyl myristate, and retinyl stearate. Most preferably, the retinol ester is retinyl palmitate.

The long-chain fatty acid ester of ascorbic acid is preferably selected from the group consisting of ascorbyl palmitate, ascorbyl myristate, and ascorbyl stearate. Most preferably, the ascorbic acid ester is ascorbyl palmitate.

Preferably, the short-chain fatty acid ester of tocopherol is selected from the group consisting of tocopheryl acetate and tocopheryl propionate. Most preferably, the short-chain fatty acid ester of tocopherol is tocopheryl acetate.

In a preferred embodiment, a composition according to the present invention comprises from about 0.001% to about 1.0% of melanin, from about 0.01% to about 2.0% of tocopheryl acetate, from about 0.01% to about 2.0% of retinyl palmitate, and from about 0.01% to about 2.0% of ascorbyl palmitate.

5. Aloe Extract

Preferably, the cosmetic composition of the present invention further comprises aloe extract, which is believed to also exert a calming and soothing effect on the skin. Preferably, the composition comprises from about 0.01% to about 2.0% of aloe extract.

6. Matricaria Extract

Another optional cosmetic component is matricaria extract. Matricaria extract is derived from wild chamomile and comprises volatile oil, anthemic acid, anthemidine, tannin, and matricarin, a tricyclic compound with the systemic name of 4-(acetyloxy)-3,3a,4,5,9a,9b-hexahydro-3,6,9-trimethylazuleno[4,5-b]furan-2,7-dione. Matricaria extract acts as a counterirritant.

Preferably, cosmetic compositions of the present invention comprise from about 0.01% to about 2.0% matricaria extract.

7. Apricot Kernel Extract

Another optional cosmetic component in compositions according to the present invention is apricot kernel extract. If present, it is preferably present in concentrations of from about 0.001% to about 1.0% of the composition.

Most preferably, cosmetic compositions according to the present invention contain aloe extract, matricaria extract, and apricot kernel extract.

The remaining optional cosmetic components disclosed below are present in particular preferred embodiments of cosmetic compositions according to the present invention.

8. Garden Balsam Leaf Extract

Another optional cosmetic component in compositions according to the present invention is garden balsam leaf extract. This plant extract is believed to exert a soothing and protective effect on the skin. When present, it is preferably present in concentrations of from about 0.01% to about 2.0%.

9. Hydrolyzed Soy Protein

Another optional cosmetic component in cosmetic compositions according to the present invention is hydrolyzed soy protein. This compound is also believed to exert a protective effect on the skin, particularly on oily skin. When present, hydrolyzed soy protein is present in a concentration of from about 0.01% to about 1.0% of the composition.

10. Horsetail Extract

Another optional cosmetic ingredient in compositions according to the present invention is horsetail extract. This compound is also believed to exert a calming and soothing effect on the skin. When present, it is preferably used in a concentration of from about 0.01% to about 2.0%.

B. The Ancillary Components

The ancillary components, whose use is optional but preferably, impart additional desirable properties to the cosmetic composition of the present invention. These ancillary components can include: (1) a solvent component; (2) a preservative component; (3) a thickener component; (4) a hydrophilic component; (5) a lipid-soluble component; and (6) pigment.

Preferred combinations of ancillary components are indicated below.

1. The Solvent Component

The skin cream composition can comprise a solvent component for greater uniformity and ease of preparation. The solvent component can include one to two ingredients, each ingredient being selected from the group consisting of butylene glycol and hexylene glycol. In one particularly preferred composition of the present invention, the solvent component comprises butylene glycol in a concentration of from about 0.1% to about 2.0%. In another preferred composition of the present invention, the solvent component comprises butylene glycol in a concentration of from about 0.1% to about 2.0% and hexylene glycol in a concentration of from about 0.1% to about 5.0%.

2. The Thickener Component

The composition can further comprise a thickener component to improve the flow and rheological properties of the cosmetic composition to retain the composition when it is applied to the skin or eyes of the wearer.

The thickener component can comprise from one to four ingredients, each ingredient being selected from the group consisting of polyacrylamide, xanthan gum, carrageenan, and silica. In one preferred embodiment of the cosmetic composition according to the present invention, the composition includes from about 0.1% to about 2.0% of polyacrylamide and from 0.01% to about 1.0% of xanthan gum as a thickener component. In another preferred composition according to the present invention, the composition includes from about 0.1% to about 2.0% of polyacrylamide, from about 0.01% to about 2.0% of carrageenan, from about 0.01% to about 1.0% of xanthan gum, and from about 0.1% to about 3.0% of silica. Other combinations of these ingredients can also be used.

3. The Hydrophilic Component

The composition can further include a hydrophilic component. The hydrophilic component can comprise from one to ten ingredients, each ingredient being selected from the group consisting of fructose, glucose, sucrose, urea, dextrin, alanine, glutamic acid, glycerin, aspartic acid, and hexyl nicotinate. In one particularly preferred cosmetic composition according to the present invention, the composition includes from about 0.1% to about 2.0% of glycerin. In another preferred composition according to the present invention, the composition includes from about 0.1% to about 2.0% of fructose, from about 0.01% to about 2.0% of glucose, from about 0.01% to about 2.0% of sucrose, from about 0.01% to about 2.0% of urea, from about 0.01% to about 2.0% of dextrin, from about 0.01% to about 2.0% of alanine, from about 0.01% to about 2.0% of glutamic acid, from about 0.01% to about 2.0% of aspartic acid, and from about 0.01% to about 2.0% of hexyl nicotinate.

4. The Preservative Component

The composition can further comprise a preservative component to retard microbial and mold growth in the composition, which is typically manufactured under clean but non-sterile conditions. The preservative component can also act as a stabilizer.

The preservative component can comprise from one to seven ingredients, each ingredient being selected from the group consisting of sodium citrate, a sodium salt of EDTA selected from the group consisting of disodium EDTA and trisodium EDTA, phenoxyethanol, chlorphenesin, methylparaben, propylparaben, and butylparaben. One preferred composition according to the present invention includes from about 0.01% to about 1.0% of sodium citrate, from about 0.01% to about 1.0% of disodium EDTA, from about 0.01% to about 1.0% of chlorphenesin, from about 0.01% to about 1.0% of methylparaben, from about 0.01% to about 1.0% of propylparaben, from about 0.01% to about 1.0% of butylparaben, and from about 0.01% to about 1.0% of phenoxyethanol. Another preferred composition according to the present invention includes from about 0.01% to about 1.0% of sodium citrate, from about 0.01% to about 1.0% of trisodium EDTA, from about 0.01% to about 1.0% of chlorphenesin, from about 0.01% to about 1.0% of methylparaben, from about 0.01% to about 1.0% of propylparaben, from about 0.01% to about 1.0% of butylparaben, and from about 0.01% to about 1.0% of phenoxyethanol.

5. The Lipid-Soluble Component

Cosmetic compositions according to the present invention can also comprise a lipid-soluble component. The lipid-soluble component can comprise from 1 to 20 ingredients, each ingredient being selected from the group consisting of: (1) neopentyl glycol dioctanoate diisostearate; (2) a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof; (3) cetearyl glucoside; (4) squalane; (5) dimethicone; (6) mineral oil; (7) cetyl alcohol; (8) steareth-2; (9) steareth-21; (10) laureth-7; (11) PEG-40 hydrogenated castor oil; (12) $C_{13}$–$C_{14}$ isoparaffin; (13) a medium-chain carboxylic acid ester of cetyl alcohol selected from the group consisting of cetyl octanoate, cetyl heptanoate, cetyl nonanoate, and mixtures thereof; (14) isodecyl oleate; (15) dicaprylyl maleate; (16) octyldodecyl neopentanoate; (17) a long-chain fatty acid ester of glycerol selected from the group consisting of glyceryl stearate, glyceryl palmitate, glyceryl arachidate, and mixtures thereof; (18) PEG-100 stearate; (19) caprylic/capric triglyceride; and (20) simethicone.

A preferred long-chain fatty acid ester of a medium-chain alcohol is octyl palmitate. A preferred medium-chain carboxylic acid ester of cetyl alcohol is cetyl octanoate. A preferred long-chain fatty acid ester of glycerol is glyceryl stearate.

The ingredients in the lipid-soluble component can be varied depending on the use of the cosmetic composition, i.e. for skin or for eyes, and also depending on whether or not the composition is formulated for normal skin, dry skin, or oily skin.

In one particularly preferred composition according to the present invention, the composition includes from about 2.0% to about 5.0% of neopentyl glycol dioctanoate diisostearate, from about 2.0% to about 5.0% of octyl palmitate, from about 1.0% to about 4.0% of cetearyl glucoside, from about 1.0% to about 3.0% of squalane, from about 1.0% to about 3.0% of dimethicone, from about 0.01% to about 2.0% of mineral oil, from about 0.1% to about 2.0% of cetyl alcohol, from about 0.18 to about 2.0% of steareth-2, from about 0.1% to about 3.0% of steareth-21, from about 0.1% to about 2.0% of laureth-7, from about 0.1% to about 2.0% of PEG-40 hydrogenated castor oil, and from about 0.1% to about 2.0% of $C_{13}$–$C_{14}$ isoparaffin.

Another preferred composition according to the present invention includes from about 1.0% to about 5.0% of cetyl octanoate, from about 1.0% to about 5.0% of isodecyl oleate, from about 1.0% to about 5.0% of dicaprylyl maleate, from about 1.0% to about 5.0% of octyldodecyl neopentanoate, from about 0.1% to about 2.0% of steareth-2, from about 0.1% to about 2.0% of steareth-21, from about 0.1% to about 2.0% of $C_{13}$–$C_{14}$ isoparaffin, from about 0.1% to about 2.0% of PEG-100 stearate, from about 0.1% to about 2.0% of cetyl alcohol, from about 0.1% to about 2.0% of laureth-7, from about 1.0% to about 3.0% of dimethicone, from about 0.1% to about 2.0% of PEG-40 hydrogenated castor oil, from about 0.01% to about 2.0% of mineral oil, and from about 0.01% to about 2.0% of simethicone.

Yet another preferred composition according to the present invention includes from about 2.0% to about 8.0% of neopentyl glycol dioctanoate diisostearate, from about 2.0% to about 8.0% of octyl palmitate, from about 1.0% to about 4.0% of cetearyl glucoside, from about 1.0% to about 3.0% of squalane, from about 1.0% to about 3.0% of dimethicone, from about 1.0% to about 8.0% of caprylic/capric triglyceride, from about 0.1% to about 2.0% of mineral oil, from about 0.1% to about 2.0% of cetyl alcohol, from about 0.1% to about 2.0% of steareth-2, from about 0.1% to about 3.0% of steareth-21, from about 0.1% to about 2.0% of laureth-7, from about 0.1% to about 2.0% of PEG-40 hydrogenated castor oil, and from about 0.1% to about 2.0% of $C_{13}$–$C_{14}$ isoparaffin.

Other combinations of ingredients for the lipid-soluble component are also within the scope of the present invention.

6. The Pigment Component

A cosmetic composition according to the present invention can further comprise a pigment component to give the cosmetic composition an aesthetically desirable appearance. The use of pigment is optional; in some compositions according to the present invention, it is not used. Preferably, the pigment is titanium dioxide. Titanium dioxide also provides protection against UV-A and UV-B radiation. In one preferred composition according to the present invention, titanium dioxide, as a pigment, comprises from about 0.01% to about 1.0% of the composition. Other pigments can be substituted for titanium dioxide depending on variables such as the skin tone of the intended user and the desired cosmetic effect.

Other ingredients commonly used in the cosmetic art such as fragrance can also be added if the desired. The addition of such components is well known in the art and need not be described further here.

For three particularly preferred cosmetic compositions according to the present invention, the preferred concentrations of both the cosmetic components and the ancillary components are shown in Tables I through III. Table I shows the preferred concentration of the cosmetic and ancillary components for the moisture lotion of Example I. Table II shows the preferred concentrations for the oil control moisture lotion of Example II. Table III shows the preferred concentrations for the moisture eye lotion of Example III. Also shown in Tables I-III are the mixtures of which each component is a part for the preparation of the composition as discussed below.

II. PREPARATION OF COSMETIC COMPOSITIONS

The various mixtures and the sequences in which they are prepared and combined for the preparation of the cosmetic compositions according to the present invention are now described in some detail. The mixtures are those referred to in Tables I through III. This sequence for combining the mixtures in preparation of the cosmetic composition is representative but not exclusive. The object of the mixing sequence is to prepare a smooth and homogeneous composition as an emulsion.

Mixture I (water) is charged into a steam-jacketed stainless-steel AGI kettle, and mixing is begun with heating to 70° C.–80° C. The ingredients in Mixture II (generally lipid-soluble components) are charged into a stainless-steel kettle equipped with a high-speed mixer such as a Lightnin'™ mixer and heated to 70° C.–80° C. When both Mixtures I and II are at the proper temperature and are uniform, Mixture II is transferred into Mixture I. Slow homogenization mixing is begun while maintaining sweep mixing. The temperature is held at 70° C.–80° C. for at least 30 minutes while mixing.

Cooling of the batch containing Mixtures I and II is then started so that the batch is cooled slowly to 45° C.–50° C. While maintaining slow cooling, the ingredients of Mixture III (propylene or butylene glycol and thickeners) are added. The combination of Mixtures I, II and III is allowed to mix for at least 15 minutes before going to the next step, the addition of the ingredients in Mixture IV. When the batch reaches 40° C., the remainder of the ingredients, those in Mixture IV, is added. These ingredients include the plant extracts, the ingredients in the micellar complex, the hydrophilic ingredients, and certain lipid-soluble ingredients, as well as the preservative components. The temperature is maintained at no lower than 35° C. while the ingredients of Mixture IV are added. The batch is allowed to mix for at least 30 minutes after the last ingredient has been added to the batch.

The batch is then cooled to 25° C.–30° C. while maintaining slow mixing. When the batch reaches the desired temperature, the batch is transferred by pump through a #200 filter bag into stainless steel containers and stored, typically at 18° C.–20° C. for cold room storage.

TABLE I

INGREDIENTS OF A PREFERRED COSMETIC COMPOSITION ACCORDING TO THE PRESENT INVENTION (MOISTURE LOTION-EXAMPLE 1)

| MIXTURE | COMPONENT | PERCENTAGE RANGE |
|---|---|---|
| I | Water | As required to dissolve other ingredients |
| II | Octyl Methoxycinnamate | 2.0–7.5 |
| II | Oxybenzone | 2.0–6.0 |
| II | Neopentyl Glycol Dioctanoate Diisostearate | 2.0–5.0 |
| II | Octyl Palmitate | 2.0–5.0 |
| II | Cetearyl Glucoside | 1.0–4.0 |
| II | Squalane | 1.0–3.0 |
| II | Dimethicone | 1.0–3.0 |
| II | Mineral Oil | 0.01–2.0 |
| II | Cetyl Alcohol | 0.1–2.0 |
| II | Steareth-2 | 0.1–2.0 |
| II | Steareth-21 | 0.1–3.0 |
| II | Laureth-7 | 0.1–2.0 |
| II | PEG-40 Hydrogenated Castor Oil | 0.1–2.0 |
| II | $C_{13}$–$C_{14}$ Isoparaffin | 0.1–2.0 |
| III | Propylene Glycol | 0.01–2.0 |
| III | Polyacrylamide | 0.1–2.0 |
| III | Xanthan Gum | 0.01–1.0 |

TABLE I-continued

INGREDIENTS OF A PREFERRED COSMETIC COMPOSITION ACCORDING TO THE PRESENT INVENTION (MOISTURE LOTION-EXAMPLE 1)

| MIXTURE | COMPONENT | PERCENTAGE RANGE |
|---|---|---|
| IV | Tocopheryl Acetate | 0.01–2.0 |
| IV | Retinyl Palmitate | 0.01–2.0 |
| IV | Ascorbyl Palmitate | 0.01–2.0 |
| IV | Melanin | 0.001–1.0 |
| IV | Hydrolyzed Wheat Protein | 0.01–1.0 |
| IV | Panthenol | 0.01–2.0 |
| IV | Garden Balsam Leaf Extract | 0.01–2.0 |
| IV | Aloe Extract | 0.01–2.0 |
| IV | Matricaria Extract | 0.01–2.0 |
| IV | Sodium Hyaluronate | 0.01–2.0 |
| IV | Phospholipids | 0.001–1.0 |
| IV | Glycosphingolipids | 0.001–1.0 |
| IV | Biotin | 0.001–1.0 |
| IV | Mannitol | 0.001–1.0 |
| IV | Glycogen | 0.001–1.0 |
| IV | Lysine Lauroyl Methionate | 0.001–1.0 |
| IV | Cholesterol | 0.001–1.0 |
| IV | Cholesteryl/Behenyl/ Octyldodecyl Lauroyl Glutamate | 0.001–1.0 |
| IV | Yeast Extract | 0.001–1.0 |
| IV | Ginseng Extract | 0.001–1.0 |
| IV | Linden Extract | 0.001–1.0 |
| IV | Apricot Kernel Extract | 0.001–1.0 |
| IV | Horse Chestnut Extract | 0.001–1.0 |
| IV | Crataegus Extract | 0.001–1.0 |
| IV | Calcium Pantothenate | 0.001–1.0 |
| IV | Sodium Pyrrolidone Carboxylic Acid | 0.1–2.0 |
| IV | Glycerin | 0.1–2.0 |
| IV | Butylene Glycol | 0.1–2.0 |
| IV | Sodium Citrate | 0.01–1.0 |
| IV | Disodium EDTA | 0.01–1.0 |
| IV | Chlorphenesin | 0.01–1.0 |
| IV | Methylparaben | 0.01–1.0 |
| IV | Propylparaben | 0.01–1.0 |
| IV | Butylparaben | 0.01–1.0 |
| IV | Phenoxyethanol | 0.01–1.0 |

TABLE II

INGREDIENTS OF A PREFERRED COSMETIC COMPOSITION ACCORDING TO THE PRESENT INVENTION (OIL CONTROL MOISTURE LOTION-EXAMPLE 2)

| MIXTURE | COMPONENT | PERCENTAGE RANGE |
|---|---|---|
| I | Water | As required to dissolve other ingredients |
| II | Octyl Methoxycinnamate | 2.0–7.5 |
| II | Oxybenzone | 2.0–6.0 |
| II | Hydrolyzed Soy Protein | 0.01–1.0 |
| II | Cetyl Octanoate | 1.0–5.0 |
| II | Isodecyl Oleate | 1.0–5.0 |
| II | Dicaprylyl Maleate | 1.0–5.0 |
| II | Octyldodecyl Neopentanoate | 1.0–5.0 |
| II | Glyceryl Stearate | 0.1–2.0 |
| II | Steareth-2 | 0.1–2.0 |
| II | Steareth-21 | 0.1–3.0 |
| II | $C_{13}$–$C_{14}$ Isoparaffin | 0.1–2.0 |

TABLE II-continued

INGREDIENTS OF A PREFERRED COSMETIC COMPOSITION ACCORDING TO THE PRESENT INVENTION (OIL CONTROL MOISTURE LOTION-EXAMPLE 2)

| MIXTURE | COMPONENT | PERCENTAGE RANGE |
|---|---|---|
| II | PEG-100 Stearate | 0.1–2.0 |
| II | Cetyl Alcohol | 0.1–2.0 |
| II | Laureth-7 | 0.1–2.0 |
| II | Dimethicone | 1.0–3.0 |
| III | Propylene Glycol | 0.01–2.0 |
| III | Polyacrylamide | 0.1–2.0 |
| III | Carrageenan | 0.01–2.0 |
| III | Xanthan Gum | 0.01–1.0 |
| IV | Silica | 0.1–3.0 |
| IV | Tocopheryl Acetate | 0.01–2.0 |
| IV | Retinyl Palmitate | 0.01–2.0 |
| IV | Ascorbyl Palmitate | 0.01–2.0 |
| IV | Melanin | 0.001–1.0 |
| IV | Hydrolyzed Wheat Protein | 0.01–2.0 |
| IV | Panthenol | 0.01–2.0 |
| IV | Aloe Extract | 0.01–2.0 |
| IV | Matricaria Extract | 0.01–2.0 |
| IV | mannitol | 0.001–1.0 |
| IV | Phospholipids | 0.001–1.0 |
| IV | Glycosphingolipids | 0.001–1.0 |
| IV | Biotin | 0.001–1.0 |
| IV | Glycogen | 0.001–1.0 |
| IV | Apricot Kernel Extract | 0.001–1.0 |
| IV | Ginseng Extract | 0.001–1.0 |
| IV | Linden Extract | 0.001–1.0 |
| IV | Yeast Extract | 0.001–1.0 |
| IV | Glycerin | 0.1–2.0 |
| IV | Horse Chestnut Extract | 0.001–1.0 |
| IV | Crataegus Extract | 0.001–1.0 |
| IV | Calcium Pantothenate | 0.001–1.0 |
| IV | Butylene Glycol | 0.1–2.0 |
| IV | Simethicone | 0.01–2.0 |
| IV | Cholesterol | 0.001–1.0 |
| IV | PEG-40 Hydrogenated Castor Oil | 0.1–2.0 |
| IV | Mineral Oil | 0.01–2.0 |
| IV | Sodium Citrate | 0.01–1.0 |
| IV | Trisodium EDTA | 0.01–1.0 |
| IV | Phenoxyethanol | 0.01–1.0 |
| IV | Chlorphenesin | 0.01–1.0 |
| IV | Methylparaben | 0.01–1.0 |
| IV | Propylparaben | 0.01–1.0 |
| IV | Butylparaben | 0.01–1.0 |
| IV | Titanium Dioxide | 0.01–1.0 |

TABLE III

INGREDIENTS OF A PREFERRED COSMETIC COMPOSITION ACCORDING TO THE PRESENT INVENTION (MOISTURE EYE LOTION-EXAMPLE 3)

| MIXTURE | COMPONENT | PERCENTAGE RANGE |
|---|---|---|
| I | Water | As required to dissolve other ingredients |
| II | Titanium Dioxide | 0.1–10.0 |
| II | Neopentyl Glycol Dioctanoate Diisostearate | 2.0–8.0 |
| II | Octyl Palmitate | 2.0–8.0 |
| II | Cetearyl Glucoside | 1.0–4.0 |
| II | Squalane | 1.0–3.0 |
| II | Dimethicone | 1.0–3.0 |
| II | Caprylic/Capric Triglyceride | 1.0–8.0 |

TABLE III-continued

INGREDIENTS OF A PREFERRED COSMETIC
COMPOSITION ACCORDING TO THE PRESENT
INVENTION (MOISTURE EYE LOTION-EXAMPLE 3)

| MIXTURE | COMPONENT | PERCENTAGE RANGE |
|---|---|---|
| II | Mineral Oil | 0.01–2.0 |
| II | Cetyl Alcohol | 0.1–2.0 |
| II | Steareth-2 | 0.1–2.0 |
| II | Steareth-21 | 0.1–3.0 |
| II | Laureth-7 | 0.1–2.0 |
| II | PEG-40 Hydrogenated Castor Oil | 0.1–2.0 |
| III | Polyacrylamide | 0.1–2.0 |
| III | Butylene Glycol | 0.1–2.0 |
| III | Xanthan Gum | 0.01–1.0 |
| IV | Tocopheryl Acetate | 0.01–2.0 |
| IV | Retinyl Palmitate | 0.01–2.0 |
| IV | Ascorbyl Palmitate | 0.01–2.0 |
| IV | Melanin | 0.001–1.0 |
| IV | Hydrolyzed Wheat Protein | 0.01–1.0 |
| IV | Panthenol | 0.01–2.0 |
| IV | Aloe Extract | 0.01–2.0 |
| IV | Matricaria Extract | 0.01–2.0 |
| IV | Phospholipids | 0.001–1.0 |
| IV | Glycosphingolipids | 0.001–1.0 |
| IV | Biotin | 0.001–1.0 |
| IV | Mannitol | 0.001–1.0 |
| IV | Glycogen | 0.001–1.0 |
| IV | Lysine Lauroyl Methionate | 0.001–1.0 |
| IV | Cholesterol | 0.001–1.0 |
| IV | Cholesteryl/Behenyl/ Octyldodecyl Lauroyl Glutamate | 0.001–1.0 |
| IV | Yeast Extract | 0.001–1.0 |
| IV | Ginseng Extract | 0.001–1.0 |
| IV | Linden Extract | 0.001–1.0 |
| IV | Apricot Kernel Extract | 0.001–1.0 |
| IV | Horse Chestnut Extract | 0.001–1.0 |
| IV | Crataegus Extract | 0.001–1.0 |
| IV | Calcium Pantothenate | 0.001–1.0 |
| IV | Propylene Glycol | 0.01–2.0 |
| IV | Hexylene Glycol | 0.1–5.0 |
| IV | Fructose | 0.01–2.0 |
| IV | Glucose | 0.01–2.0 |
| IV | Sucrose | 0.01–2.0 |
| IV | Urea | 0.01–2.0 |
| IV | Dextrin | 0.01–2.0 |
| IV | Alanine | 0.01–2.0 |
| IV | Glutamic Acid | 0.01–2.0 |
| IV | Aspartic Acid | 0.01–2.0 |
| IV | Hexyl Nicotinate | 0.01–2.0 |
| IV | Horsetail Extract | 0.01–2.0 |
| IV | $C_{13}$–$C_{14}$ Isoparaffin | 0.1–2.0 |
| IV | Glycerin | 0.1–2.0 |
| IV | Sodium Citrate | 0.01–1.0 |
| IV | Disodium EDTA | 0.01–1.0 |
| IV | Chlorphenesin | 0.01–1.0 |
| IV | Methylparaben | 0.01–1.0 |
| IV | Propylparaben | 0.01–1.0 |
| IV | Butylparaben | 0.01–1.0 |
| IV | Phenoxyethanol | 0.01–1.0 |

EXAMPLES

The invention is illustrated by the following Examples. These Examples are presented for illustrative purposes only and are not intended to limit the invention.

Example 1

Moisture Lotion

A moisture lotion for use on the skin was prepared as described above using the ingredients in Table I.

Example 2

Oil Control Moisture Lotion

An oil control moisture lotion for use on the skin was prepared as described above using the ingredients given in Table II.

Example 3

Moisture Eye Lotion

A moisture eye lotion was prepared as described above using the ingredients in Table III. This lotion omits the anti-actinic complex, but includes titanium dioxide as a sunscreen to provide protection against UV-A and UV-B radiation.

ADVANTAGES OF THE INVENTION

Cosmetic compositions according to the present invention provide significantly improved moisturization, free radical and ultraviolet light protection, while, for the first time, innovatively providing significant protection against several specific pollutants in the environment. In particular, the anti-pollution complex reduces the damaging effect of hydrogen chloride by 25%, of formaldehyde by 10%, of chloroform by 49%, of anoxia by 235%, of sulfur dioxide by 31%, of carbon monoxide by 73%, of tobacco smoke by 80%, of car exhaust fumes by 35%, and of nitrogen dioxide by 45%. The compositions of the present invention are suitable for prolonged and repeated use, and act to sooth and protect the skin.

Although the present invention has been described in considerable detail with respect to certain preferred versions thereof, other versions are possible. Therefore, the spirit and scope of the appended claims should not be limited to the descriptions of the preferred versions contained herein.

I claim:

1. A cosmetic composition comprising: water, and emulsified and dispersed in the water:

(a) an anti-pollution complex comprising propylene glycol, hydrolyzed wheat protein, mannitol, glycogen, yeast extract, ginseng extract, linden extract, calcium pantothenate, horse chestnut extract, and biotin;

(b) a micellar complex comprising: phospholipids, glycosphingolipids, panthenol, cholesterol, Crataegus extract, and sodium hyaluronate;

(c) an anti-free radical complex comprising melanin, a short-chain fatty acid ester of tocopherol, a long-chain fatty acid ester of retinol, and a long-chain fatty acid ester of ascorbic acid; and (d) a sunscreen;

the anti-pollution complex, the micellar complex, and the anti-free radical complex each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

2. The cosmetic composition of claim 1 wherein the micellar complex further includes sodium pyrrolidone carboxylic acid.

3. The cosmetic composition of claim 1 wherein the micellar complex further includes from one to two components selected from the group consisting of cholesteryl/behenyl/octyldodecyl lauroyl glutamate and lysine lauroyl methionate.

4. The cosmetic composition of claim 3 wherein the micellar complex further includes cholesteryl/behenyl/octyldodecyl lauroyl glutamate and lysine lauroyl methionate.

5. The cosmetic composition of claim 4 wherein the micellar complex further includes pyrrolidone carboxylic acid.

6. The cosmetic composition of claim 1 wherein the sunscreen comprises an anti-actinic complex comprising oxybenzone and a medium-chain methoxycinnamate ester selected from the group consisting of octyl methoxycinnamate, heptyl methoxycinnamate, nonyl methoxycinnamate, and mixtures thereof.

7. The cosmetic composition of claim 1 wherein the sunscreen comprises titanium dioxide.

8. The cosmetic composition of claim 1 further comprising aloe extract in a quantity sufficient to detectably reduce the damaging effect of environmental pollutants on the skin of a wearer to whom the composition is applied.

9. The cosmetic composition of claim 1 further comprising matricaria extract in a quantity sufficient to detectably reduce the damaging effect of environmental pollutants on the skin of a wearer to whom the composition is applied.

10. The cosmetic composition of claim 1 further comprising apricot kernel extract in a quantity sufficient to detectably reduce the damaging effect of environmental pollutants on the skin of a wearer to whom the composition is applied.

11. The cosmetic composition of claim 1 further comprising garden balsam leaf extract in a quantity sufficient to detectably reduce the damaging effect of environmental pollutants on the skin of a wearer to whom the composition is applied.

12. The cosmetic composition of claim 1 further comprising hydrolyzed soy protein in a quantity sufficient to detectably reduce the damaging effect of environmental pollutants on the skin of a wearer to whom the composition is applied.

13. The cosmetic composition of claim 1 further comprising horsetail extract in a quantity sufficient to detectably reduce the damaging effect of environmental pollutants on the skin of a wearer to whom the composition is applied.

14. The cosmetic composition of claim 1 further comprising aloe extract, matricaria extract, apricot kernel extract, and garden balsam leaf extract, each in a quantity sufficient to detectably reduce the damaging effect of environmental pollutants on the skin of a wearer to whom the composition is applied.

15. The cosmetic composition of claim 1 further comprising aloe extract, matricaria extract, apricot kernel extract, and hydrolyzed soy protein, each in a quantity sufficient to detectably reduce the damaging effect of environmental pollutanns on the skin of a wearer to whom the composition is applied.

16. The cosmetic composition of claim 6 further comprising aloe extract, matricaria extract, apricot kernel extract, and garden balsam leaf extract, each in a quantity sufficient to detectably reduce the damaging effect of environmental pollutants on the skin of a wearer to whom the composition is applied.

17. The cosmetic composition of claim 6 further comprising aloe extract, matricaria extract, apricot kernel extract, and hydrolyzed soy protein, each in a quantity sufficient to detectably reduce the damaging effect of environmental pollutants on the skin of a wearer to whom the composition is applied.

18. The cosmetic composition of claim 7 further comprising aloe extract, matricaria extract, and apricot kernel extract, each in a quantity sufficient to detectably reduce the damaging effect of environmental pollutants on the skin of a wearer to whom the composition is applied.

19. The skin cream composition of claim 1 wherein the retinol ester is selected from the group consisting of retinyl palmitate, retinyl myristate, and retinyl stearate.

20. The skin cream composition of claim 19 wherein the retinol ester is retinyl palmitate.

21. The cosmetic composition of claim 1 wherein the ascorbic acid ester is selected from the group consisting of ascorbyl palmitate, ascorbyl myristate, and ascorbyl stearate.

22. The cosmetic composition of claim 21 wherein the ascorbic acid ester is ascorbyl palmitate.

23. The cosmetic composition of claim 1 wherein the tocopherol ester is selected from the group consisting of tocopheryl acetate and tocopheryl propionate.

24. The cosmetic composition of claim 22 wherein the tocopherol ester is tocopheryl acetate.

25. The cosmetic composition of claim 1 further comprising a solvent component.

26. The cosmetic composition of claim 25 wherein the solvent component comprises from one to two ingredients, each ingredient being selected from the group consisting of butylene glycol and hexylene glycol.

27. The cosmetic composition of claim 26 wherein the solvent component comprises butylene glycol.

28. The cosmetic composition of claim 26 wherein the solvent component comprises butylene glycol and hexylene glycol.

29. The cosmetic composition of claim 1 further comprising a lipid-soluble component.

30. The cosmetic composition of claim 29 wherein the lipid-soluble component comprises from 1 to 20 ingredients, each ingredient being selected from the group consisting of (1) neopentyl glycol dioctanoate diisostearate; (2) a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, nonyl stearate, and mixtures thereof; (3) cetearyl glucoside; (4) squalane; (5) dimethicone; (6) mineral oil; (7) cetyl alcohol; (8) steareth-2; (9) steareth-21; (10) laureth-7; (11) PEG-40 hydrogenated castor oil; (12) $C_{13}$–$C_{14}$ isoparaffin; (13) a medium-chain carboxylic acid ester of cetyl alcohol selected from the group consisting of cetyl octanoate, cetyl heptanoate, cetyl nonanoate, and mixtures thereof; (14) isodecyl oleate; (15) dicaprylyl maleate; (16) octyldodecyl neopentanoate; (17) a long-chain fatty acid ester of glycerol selected from the group consisting of glyceryl stearate, glyceryl palmitate, glyceryl arachidate, and mixtures thereof; (18) PEG-100 stearate; (19) caprylic/capric triglyceride; and (20) simethicone.

31. The cosmetic composition of claim 30 wherein the lipid-soluble component comprises neopentyl glycol dioctanoate diisostearate, octyl palmitate, cetearyl glucoside, squalane, dimethicone, mineral oil, cetyl alcohol, steareth-2, steareth-21, laureth-7, PEG-40 hydrogenated castor oil, and $C_{13}$–$C_{14}$ isoparaffin.

32. The cosmetic composition of claim 30 wherein the lipid-soluble component comprises cetyl octanoate, isodecyl oleate, dicaprylyl maleate, octyldodecyl neopentanoate, glyceryl stearate, steareth-2, steareth-21, $C_{13}$–$C_{14}$ isoparaffin, PEG-100 stearate, cetyl alcohol, laureth-7, dimethicone, simethicone, PEG-40 hydrogenated castor oil, and mineral oil.

33. The cosmetic composition of claim 30 wherein the lipid-soluble component comprises neopentyl glycol dioctanoate diisostearate, octyl palmitate, cetearyl glucoside, squalane, dimethicone, caprylic/capric triglyceride, mineral oil, cetyl alcohol, steareth-2, steareth-21, laureth-7, and PEG-40 hydrogenated castor oil.

34. The cosmetic composition of claim 1 further comprising a thickener component.

35. The cosmetic composition of claim 34 wherein the thickener component comprises from one to four ingredients, each ingredient selected from the group consisting of polyacrylamide, carrageenan, xanthan gum, and silica.

36. The cosmetic composition of claim 35 wherein the thickener component comprises polyacrylamide and xanthan gum.

37. The cosmetic composition of claim 35 wherein the thickener component comprises polyacrylamide, carrageenan, xanthan gum and silica.

38. The cosmetic composition of claim 1 further comprising a pigment component.

39. The cosmetic composition of claim 38 wherein the pigment is titanium dioxide.

40. The cosmetic composition of claim 1 further comprising a hydrophilic component.

41. The cosmetic composition of claim 40 wherein the hydrophilic component comprises from 1 to 10 ingredients, each ingredient being selected from the group consisting of fructose, glucose, sucrose, urea, dextrin, alanine, glutamic acid, glycerin, aspartic acid, and hexyl nicotinate.

42. The cosmetic composition of claim 40 wherein the hydrophilic component comprises glycerin.

43. The cosmetic composition of claim 40 wherein the hydrophilic component comprises glycerin, fructose, glucose, sucrose, urea, dextrin, alanine, glutamic acid, aspartic acid, and hexyl nicotinate.

44. The cosmetic composition of claim 1 further comprising a preservative component.

45. The cosmetic composition of claim 44 wherein the preservative component comprises from 1 to 7 ingredients, each ingredient being selected from the group consisting of sodium citrate, a sodium salt of EDTA selected from the group consisting of disodium EDTA and trisodium EDTA, phenoxyethanol, chlorphenesin, methylparaben, propylparaben, and butylparaben.

46. The cosmetic composition of claim 44 wherein the preservative component comprises sodium citrate, disodium EDTA, chlorphenesin, methylparaben, propylparaben, butylparaben, and phenoxyethanol.

47. The cosmetic composition of claim 44 wherein the preservative component comprises sodium citrate, trisodium EDTA, phenoxyethanol, chlorphenesin, methylparaben, propylparaben, and butylparaben.

48. A cosmetic composition comprising: water, and emulsified and dispersed in the water:

(a) an anti-pollution complex comprising propylene glycol, hydrolyzed wheat protein, mannitol, glycogen, yeast extract, ginseng extract, linden extract, calcium pantothenate, horse chestnut extract, and biotin;

(b) a micellar complex comprising: phospholipids, glycosphingolipids, Crataegus extract, sodium hyaluronate, sodium pyrrolidone carboxylic acid, cholesterol, cholesteryl/behenyl/octyldodecyl lauroyl glutamate, lysine lauroyl methionate, and panthenol;

(c) a sunscreen comprising an anti-actinic complex, the anti-actinic complex comprising octyl methoxycinnamate and oxybenzone;

(d) an anti-free radical complex comprising melanin, tocopheryl acetate, retinyl palmitate, and ascorbyl palmitate;

(e) garden balsam leaf extract;

(f) aloe extract;

(g) matricaria extract; and (h) apricot kernel extract; the anti-pollution complex, the micellar complex, the anti-free radical complex, the garden balsam leaf extract, the aloe extract, the matricaria extract, and the apricot kernel extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

49. The cosmetic composition of claim 48 wherein the propylene glycol comprises from about 0.01% to about 2.0% of the composition, the hydrolyzed wheat protein comprises from about 0.01% to about 1.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0% of the composition, the biotin comprises from about 0.001% to about 1.0% of the composition, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the sodium hyaluronate comprises from about 0.01% to about 2.0% of the composition, the sodium pyrrolidone carboxylic acid comprises from about 0.1% to about 2.0% of the composition, the cholesterol comprises from about 0.001% to about 1.0% of the composition, the cholesteryl/behenyl/octyldodecyl lauroyl glutamate comprises from about 0.001% to about 1.0% of the composition, the panthenol comprises from about 0.01% to about 2.0% of the composition, the octyl methoxycinnamate comprises from about 2.0% to about 7.5% of the composition, the oxybenzone comprises from about 2.0% to about 6.0% of the composition, the melanin comprises from about 0.001% to about 1.0% of the composition, the tocopheryl acetate comprises from about 0.01% to about 2.0% of the composition, the retinyl palmitate comprises from about 0.01% to about 2.0% of the composition, the ascorbyl palmitate comprises from about 0.01% to about 2.0% of the composition, the garden balsam leaf extract comprises from about 0.01% to about 2.0% of the composition, the aloe extract comprises from about 0.01% to about 2.0% of the composition, the matricaria extract comprises from about 0.01% to about 2.0% of the composition, and the apricot kernel extract comprises from about 0.001% to about 1.0% of the composition.

50. A cosmetic composition comprising: water, and emulsified and dispersed in the water:
  (a) an anti-pollution complex comprising propylene glycol, hydrolyzed wheat protein, mannitol, glycogen, yeast extract, ginseng extract, linden extract, calcium pantothenate, horse chestnut extract, and biotin;
  (b) a micellar complex comprising: phospholipids, glycosphingolipids, panthenol, Crataegus extract, and cholesterol;
  (c) a sunscreen comprising an anti-actinic complex, the anti-actinic complex comprising octyl methoxycinnamate and oxybenzone;
  (d) an anti-free radical complex comprising melanin, tocopheryl acetate, retinyl palmitate, and ascorbyl palmitate;
  (e) hydrolyzed soy protein;
  (f) aloe extract;
  (g) matricaria extract; and
  (h) apricot kernel extract;
the anti-pollution complex, the micellar complex, the anti-free radical complex, the hydrolyzed soy protein, the aloe extract, the matricaria extract, and the apricot kernel extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

51. The cosmetic composition of claim 50 wherein the propylene glycol comprises from about 0.01% to about 2.0% of the composition, the hydrolyzed wheat protein comprises from about 0.01% to about 2.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0% of the composition, the biotin comprises from about 0.001% to about 1.0% of the composition, the phospholipids comprise from about 0.001% to about 1.0% of the composition, the glycosphingolipids comprise from about 0.001% of the composition to about 1.0% of the composition, the Crataegus extract comprises from about 0.001% to about 1.0% of the composition, the cholesterol comprises from about 0.001% to about 1.0% of the composition, the panthenol comprises from about 0.01% to about 2.0% of the composition, the octyl methoxycinnamate comprises from about 2.0% to about 7.5% of the composition, the oxybenzone comprises from about 2.0% to about 6.0% of the composition, the melanin comprises from about 0.001% to about 1.0% of the composition, the tocopheryl acetate comprises from about 0.01% to about 2.0% of the composition, the retinyl palmitate comprises from about 0.01% to about 2.0% of the composition, the ascorbyl palmitate comprises from about 0.01% to about 2.0% of the composition, the hydrolyzed soy protein comprises from about 0.01% to about 1.0% of the composition, the aloe extract comprises from about 0.01% to about 2.0% of the composition, the matricaria extract comprises from about 0.01% to about 2.0% of the composition, and the apricot kernel extract comprises from about 0.001% to about 1.0% of the composition.

52. A cosmetic composition comprising: water, and emulsified and dispersed in the water:
  (a) an anti-pollution complex comprising propylene glycol, hydrolyzed wheat protein, mannitol, glycogen, yeast extract, ginseng extract, linden extract, calcium pantothenate, horse chestnut extract, and biotin;
  (b) a micellar complex comprising phospholipids, glycosphingolipids, Crataegus extract, panthenol, cholesterol, cholesteryl/behenyl/octyldodecyl lauroyl glutamate, and lysine lauroyl methionate;
  (c) a sunscreen comprising titanium dioxide;
  (d) an anti-free radical complex comprising melanin, tocopheryl acetate, retinyl palmitate, and ascorbyl palmitate;
  (e) aloe extract;
  (f) apricot kernel extract; and
  (g) horsetail extract;
the anti-pollution complex, the micellar complex, the anti-free radical complex, the aloe extract, the matricaria extract, and the apricot kernel extract, and the horsetail extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

53. The cosmetic composition of claim 52 wherein the propylene glycol comprises from about 0.01% to about 2.0% of the composition, the hydrolyzed wheat protein comprises from about 0.01% to about 1.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0% of the composition, the biotin comprises from about 0.001% to about 1.0% of the composition, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the panthenol comprises from about 0.01% to about 2.0% of the composition, the cholesterol comprises from about 0.001% to about 1.0% of the composition, the cholesteryl/behenyl/octyldodecyl lauroyl glutamate comprises from about 0.001% to about 1.0% of the composition, the lysine lauroyl methionate comprises from about 0.001% to about 1.0% of the composition, the titanium dioxide comprises from about 0.1% to about 10% of the composition, the melanin comprises from about 0.001% to about 1.0% of the composition, the tocopheryl acetate comprises from about 0.01% to about 2.0% of the composition, the retinyl palmitate comprises from about 0.01% to about 2.0% of the composition, the ascorbyl palmitate comprises from about 0.01% to about 2.0% of the composition, the aloe extract comprises from about 0.01% to about 2.0% of the composition, the matricaria extract comprises from about 0.01% to about 2.0% of the composition, the apricot kernel extract comprises from about 0.001% to about 1.0% of the composition, and the horsetail extract comprises from about 0.01% to about 2.0% of the composition.

54. A cosmetic composition comprising: water, and emulsified and dispersed in the water:
(a) an anti-pollution complex comprising:
  (i) propylene glycol;
  (ii) hydrolyzed wheat protein;
  (iii) mannitol;
  (iv) glycogen;
  (v) yeast extract;
  (vi) ginseng extract;
  (vii) linden extract;
  (viii) calcium pantothenate;
  (ix) horse chestnut extract; and
  (x) biotin;
(b) a micellar complex comprising:
  (i) phospholipids;
  (ii) glycosphingolipids;
  (iii) Crataegus extract;
  (iv) sodium hyaluronate;
  (v) sodium pyrrolidone carboxylic acid;
  (vi) panthenol:
  (vii) cholesterol;
  (viii) cholesteryl/behenyl/octyldodecyl lauroyl glutamate; and
  (ix) lysine lauroyl methionate;
(c) a sunscreen comprising an anti-actinic complex, the anti-actinic complex comprising:
  (i) octylmethoxycinnamate; and
  (ii) oxybenzone;
(d) an anti-free radical complex comprising:
  (i) melanin;
  (ii) tocopheryl acetate;
  (iii) retinyl palmitate; and
  (iv) ascorbyl palmitate;
(e) aloe extract;
(f) matricaria extract;
(g) apricot kernel extract;
(h) garden balsam leaf extract;
(i) neopentyl glycol dioctanoate diisostearate; octyl palmitate;
(k) cetearyl glucoside;
(l) squalane;
(m) dimethicone;
(n) mineral oil;
(o) cetyl alcohol;
(p) steareth-2;
(q) steareth-21;
(r) laureth-7;
(s) PEG-40 hydrogenated castor oil;
(t) $C_{13}$–$C_{14}$ isoparaffin;
(u) propylene glycol;
(v) polyacrylamide;
(w) xanthan gum;
(x) glycerin;
(y) butylene glycol;
(z) sodium citrate;
(aa) disodium EDTA;
(ab) chlorphenesin;
(ac) methylparaben;
(ad) propylparaben;
(ae) butylparaben; and
(af) phenoxyethanol;
the anti-pollution complex, the micellar complex, the anti-free radical complex, the aloe extract, the matricaria extract, the apricot kernel extract, and the garden balsam leaf extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

55. The cosmetic composition of claim 54 wherein the propylene glycol comprises from about 0.01% to about 2.0% of the composition, the hydrolyzed wheat protein comprises from about 0.001% to about 1.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0% of the composition, the biotin comprises from about 0.001% to about 1.0% of the composition, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the sodium hyaluronate comprises from about 0.01% to about 2.0% of the composition, the sodium pyrrolidone carboxylic acid comprises from about 0.1% to about 2.0% of the composition, the cholesterol comprises from about 0.001% to about 1.0% of the composition, the cholesteryl/behenyl/octyldodecyl lauroyl glutamate comprises from about 0.001% to about 1.0% of the composition, the panthenol comprises from about 0.01% to about 2.0% of the composition, the octyl methoxycinnamate comprises from about 2.0% to about 7.5% of the composition, the oxybenzone comprises from about 2.0% to about 6.0% of the composition, the melanin comprises from about 0.001% to about 1.0% of the composition, the tocopheryl acetate comprises from about 0.01% to about 2.0% of the composition, the retinyl palmitate comprises from about 0.01% to about 2.0% of the composition, the ascorbyl palmitate comprises from about 0.01% to about 2.0% of the composition, the garden balsam leaf extract comprises from about 0.01% to about 2.0% of the composition, the aloe extract comprises from about 0.01% to about 2.0% of the composition, the matricaria extract comprises from about 0.01% to about 2.0% of the composition, and the apricot kernel extract comprises from about 0.001% to about 1.0% of the composition.

56. A cosmetic composition comprising: watery and emulsified and dispersed in the water:
(a) an anti-pollution complex comprising:
  (i) propylene glycol;
  (ii) hydrolyzed wheat protein;
  (iii) mannitol;
  (iv) glycogen;
  (v) yeast extract;
  (vi) ginseng extract;
  (vii) linden extract;

(viii) calcium pantothenate;
(ix) horse chestnut extract; and
(x) biotin;
(b) a micellar complex comprising:
(i) phospholipids;
(ii) glycosphingolipids;
(iii) panthenol;
(iv) Crataegus extract; and
(v) cholesterol;
(c) a sunscreen comprising an anti-actinic complex, the anti-actinic complex comprising:
(i) octyl methoxycinnamate; and
(ii) oxybenzone;
(d) an anti-free radical complex comprising:
(i) melanin;
(ii) tocopheryl acetate;
(iii) retinyl palmitate; and
(iv) ascorbyl palmitate;
(e) hydrolyzed soy protein;
(f) aloe extract
(g) matricaria extract;
(h) apricot kernel extract;
(i) cetyl octanoate;
(j) isodecyl oleate;
(k) dicaprylyl maleate;
(l) octyldodecyl neopentanoate;
(m) glyceryl stearate;
(n) steareth-2;
(o) steareth-21;
(p) $C_{13}$–$C_{14}$ isoparaffin;
(q) PEG-100 stearate;
(r) cetyl alcohol;
(s) laureth-7;
(t) dimethicone;
(u) polyacrylamide;
(v) carrageenan;
(w) xanthan gum;
(x) silica;
(y) glycerin;
(z) butylene glycol;
(aa) simethicone;
(ab) PEG-40 hydrogenated castor oil;
(ac) mineral oil;
(ad) sodium citrate;
(ae) trisodium EDTA;
(af) phenoxyethanol;
(ag) chlorphenesin;
(ah) methylparaben;
(ai) propylparaben; and
(aj) titanium dioxide;
the anti-pollution complex, the micellar complex, the anti-free radical complex, the hydrolyzed soy protein, the aloe extract, and the apricot kernel extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

57. The cosmetic composition of claim 56 wherein the propylene glycol comprises from about 0.01% to about 2.0% of the composition, the hydrolyzed wheat protein comprises from about 0.01% to about 2.0% of the composition, the mannitol comprises from about 0.001% to about 1.0% of the composition, the glycogen comprises from about 0.001% to about 1.0% of the composition, the yeast extract comprises from about 0.001% of the composition to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0% of the composition, the biotin comprises from about 0.001% to about 1.0% of the composition, the phospholipids comprise from about 0.001% to about 1.0% of the composition, the glycosphingolipids comprise from about 0.001% of the composition to about 1.0% of the composition, the Crataegus extract comprises from about 0.001% to about 1.0% of the composition, the panthenol comprises from about 0.01% to about 2.0% of the composition, the cholesterol comprises from about 0.001% to about 1.0% of the composition, the octyl methoxycinnamate comprises from about 2.0% to about 7.5% of the composition, the oxybenzone comprises from about 2.0% to about 6.0% of the composition, the melanin comprises from about 0.001% to about 1.0% of the composition, the tocopheryl acetate comprises from about 0.01% of the composition to about 2.0% of the composition, the retinyl palmitate comprises from about 0.01% of the composition to about 2.0% of the composition, the ascorbyl palmitate comprises from about 0.01% of the composition to about 2.0% of the composition, the hydrolyzed soy protein comprises from about 0.01% to about 1.0% of the composition, the aloe extract comprises from about 0.01% of the composition to about 2.0% of the composition, the matricaria extract comprises from about 0.01% of the composition to about 2.0% of the composition, and the apricot kernel extract comprises from about 0.001% of the composition to about 1.0% of the composition.

58. A cosmetic composition comprising: water, and emulsified and dispersed in the water:
(a) an anti-pollution complex comprising:
(i) propylene glycol;
(ii) hydrolyzed wheat protein;
(iii) mannitol;
(iv) glycogen;
(v) yeast extract;
(vi) ginseng extract;
(vii) linden extract;
(viii) calcium pantothenate;
(ix) horse chestnut extract; and
(x) biotin;
(b) a micellar complex comprising:
(i) phospholipids;
(ii) glycosphingolipids;
(iii) panthenol;
(iv) Crataegus extract; and
(v) cholesterol;
(vi) cholesteryl/behenyl/octyldodecyllauroyl glutamate;
(viii) lysine lauroyl methionate;
(c) a sunscreen comprising titanium dioxide;
(d) an anti-free radical complex comprising:
(i) melanin;
(ii) tocopheryl acetate;
(iii) retinyl palmitate; and (iv) ascorbyl palmitate;
(e) aloe extract;
(f) matricaria extract;
(g) apricot kernel extract;
(h) horsetail extract;
(i) neopentyl glycol dioctanoate diisostearate;
(j) octyl palmitate;
(k) cetearyl glucoside;
(l) squalane;
(m) dimethicone;
(n) caprylic/capric triglyceride;
(o) mineral oil;
(p) cetyl alcohol;
(q) steareth-2;
(r) steareth-21;
(s) laureth-7;
(t) PEG-40 hydrogenated castor oil;
(u) polyacrylamide;
(v) butylene glycol;
(w) xanthan gum;
(x) hexylene glycol;
(y) fructose;
(z) glucose;
(aa) sucrose;
(ab) urea;
(ac) dextrin;
(ad) alanine;
(ae) glutamic acid;
(af) aspartic acid;
(ag) hexyl nicotinate;
(ah) $C_{13}$–$C_{14}$ isoparaffin;
(ai) glycerin;
(aj) sodium citrate;
(ak) disodium EDTA;
(al) chlorphenesin;
(am) methylparaben;
(an) propylparaben;
(ao) butylparaben; and
(ap) phenoxyethanol;
the anti-pollution complex, the micellar complex, the anti-free radical complex, the aloe extract, the matricaria extract, and the horsetail extract each being present in a quantity sufficient to detectably reduce the damaging effect of at least one environmental stress selected from the group consisting of environmental pollutants, moisture loss, and free radical activity on the skin of a wearer to whom the composition is applied, and the sunscreen being present in a quantity sufficient to protect the skin against at least one of UV-A and UV-B solar radiation.

59. The cosmetic composition of claim 58 wherein the propylene glycol comprises from about 0.01% to about 2.0% of the composition, the hydrolyzed wheat protein comprises from about 0.01% to about 1.0% of the composition, the mannitol comprises from about 0.001% to about 1.0% of the composition, the glycogen comprises from about 0.001% to about 1.0% of the composition, the yeast extract comprises from about 0.001% to about 1.0% of the composition, the ginseng extract comprises from about 0.001% to about 1.0% of the composition, the linden extract comprises from about 0.001% to about 1.0% of the composition, the calcium pantothenate comprises from about 0.001% to about 1.0% of the composition, the horse chestnut extract comprises from about 0.001% to about 1.0 of the composition, the biotin comprises from about 0.001% to about 1.0% of the composition, the phospholipids comprise from about 0.001% to about 1.0% of the composition, the glycosphingolipids comprise from about 0.001% to about 1.0% of the composition, the Crataegus extract comprises from about 0.001% to about 1.0% of the composition, the panthenol comprises from about 0.01% to about 2.0% of the composition, the cholesterol comprises from about 0.001% to about 1.0% of the composition, the cholesteryl/behenyl/octyldodecyl lauroyl glutamate comprises from about 0.001% to about 1.0% of the composition, the lysine lauroyl methionate comprises from about 0.001% to about 1.0% of the composition, the titanium dioxide comprises from about 0.1% to about 10% of the composition, the melanin comprises from about 0.001% to about 1.0% of the composition, the tocopheryl acetate comprises from about 0.01% to about 2.0% of the composition, the retinyl palmitate comprises from about 0.01% to about 2.0% of the composition, the ascorbyl palmitate comprises from about 0.01% to about 2.0% of the composition, the aloe extract comprises from about 0.01% to about 2.0% of the composition, the matricaria extract comprises from about 0.01% of the composition to about 2.0% of the composition, and the horsetail extract comprises from about 0.01% to about 2.0% of the composition.

60. A cosmetic composition comprising: water and emulsified and dispersed in the water:
(a) about 0.01% to about 2.0% of propylene glycol;
(b) about 0.01% to about 1.0% of hydrolyzed wheat protein;
(c) about 0.001% to about 1.0% of mannitol;
(d) about 0.001% to about 1.0% of glycogen;
(e) about 0.001% to about 1.0% of yeast extract;
(f) about 0.001% to about 1.0% of ginseng extract;
(g) about 0.001% to about 1.0% of linden extract;
(h) about 0.001% to about 1.0% of calcium pantothenate;
(i) about 0.001% to about 1.0% of horse chestnut extract;
(j) about 0.001% to about 1.0% of biotin;
(k) about 0.001% to about 1.0% of phospholipids;
(l) about 0.001% to about 1.0% of glycosphingolipids;
(m) about 0. 001% to about 1.0% of Crataegus extract;
(n) about 0.01% to about 2.0% of panthenol;
(o) about 0.01% to about 2.0% of sodium hyaluronate;
(p) about 0.1% to about 2.0% of sodium pyrrolidone carboxylic acid;
(q) about 0.001% to about 1.0% of cholesterol;
(r) about 0.001% to about 1.0% of cholesteryl/behenyl/octyldodecyl lauroyl glutamate;
(s) about 0.001% to about 1.0% of lysine lauroyl methionate
(t) about 0.001% to about 1.0% of melanin;
(u) about 0.01% to about 2.0% of tocopheryl acetate;
(v) about 0.01% to about 2.0% of retinyl palmitate;
(w) about 0.01% to about 2.0% of ascorbyl palmitate;
(x) about 0.01% to about 2.0% of aloe extract;
(y) about 0.01% to about 2.0% of matricaria extract;
(z) about 0.001% to about 1.0% of apricot kernel extract;
(aa) about 0.01% to about 2.0% of garden balsam leaf extract;
(ab) about 2.0% to about 7.5% of octyl methoxycinnamate;

(ac) about 2.0% to about 6.0% of oxybenzone;
(ad) about 2.0% to about 5.0% of neopentyl glycol dioctanoate diisostearate;
(ae) about 2.0% to about 5.0% of octyl palmitate;
(af) about 1.0% to about 4.0% of cetearyl glucoside;
(ag) about 1.0% to about 3.0% of squalane;
(ah) about 1.0% to about 3.0% of dimethicone;
(ai) about 0.01% to about 2.0% of mineral oil;
(aj) about 0.1% to about 2.0% of cetyl alcohol;
(ak) about 0.1% to about 2.0% of steareth-2;
(al) about 0.1% to about 3.0% of steareth-21;
(am) about 0.1% to about 2.0% of laureth-7;
(an) about 0.1% to about 2.0% of PEG-40 hydrogenated castor oil;
(ao) about 0.1% to about 2.0% of $C_{13}$–$C_{14}$ isoparaffin;
(ap) about 0.1% to about 2.0% of polyacrylamide;
(aq) about 0.1% to about 2.0% of butylene glycol;
(ar) about 0.01% to about 1.0% of sodium citrate;
(as) about 0.01% to about 1.0% of disodium EDTA;
(at) about 0.01% to about 1.0% of chlorphenesin;
(au) about 0.01% to about 1.0% of methylparaben;
(av) about 0.01% to about 1.0% of propylparaben;
(ax) about 0.01% to about 1.0% of butylparaben; and
(ay) about 0.01% no about 1.0% of phenoxyethanol;
wherein the propylene glycol, the hydrolyzed wheat protein, the mannitol, the glycogen, the yeast extract, the ginseng extract, the linden extract, the calcium pantothenate, the horse chestnut extract, and the biotin comprise an anti-pollution complex, the phospholipids, the glycosphingolipids, the Crataegus extract, the sodium hyaluronate, the sodium pyrrolidone carboxylic acid, the panthenol, the cholesterol, the cholesteryl/behenyl/octyldodecyl lauroyl glutamate and the lysine lauroyl methionate comprise a micellar complex, the octyl methoxycinnamate and the oxybenzone comprise an anti-actinic complex, and the melanin, the tocopheryl acetate, the retinyl palmitate, and the ascorbyl palmitate comprise an anti-free radical complex.

61. A cosmetic composition comprising: water, and emulsified and dispersed in the water:
(a) about 0.01% to about 2.0% of propylene glycol;
(b) about 0.01% to about 2.0% of hydrolyzed wheat protein;
(c) about 0.001% to about 1.0% of mannitol;
(d) about 0.001% to about 1.0% of glycogen;
(e) about 0.001% to about 1.0% of yeast extract;
(f) about 0.001% to about 1.0% of ginseng extract;
(g) about 0.001% to about 1.0% of linden extract;
(h) about 0.001% to about 1.0% of calcium pantothenate;
(i) about 0.001% to about 1.0% of horse chestnut extract;
(j) about 0.001% to about 1.0% of biotin;
(k) about 0.001% to about 1.0% of phospholipids;
(l) about 0.001% to about 1.0% of glycosphingolipids;
(m) about 0.01% to about 2.0% of panthenol;
(n) about 0.001% to about 1.0% of Crataegus extract;
(o) about 0.001% to about 1.0% of cholesterol;
(p) about 2.0% to about 7.5% of octyl methoxycinnamate;
(q) about 2.0% to about 6.0% of oxybenzone;
(r) about 0.001% to about 1.0% of melanin;
(s) about 0.01% to about 2.0% of tocopheryl acetate;
(t) about 0.01% to about 2.0% of retinyl palmitate;
(u) about 0.01% to about 2.0% of ascorbyl palmitate;
(v) about 0.01% to about 2.0% of aloe extract;
(w) about 0.01% to about 2.0% of matricaria extract;
(x) about 0.001% to about 1.0% of apricot kernel extract;
(y) about 0.01% to about 1.0% of hydrolyzed soy protein;
(z) about 1.0% to about 5.0% of cetyl octanoate;
(aa) about 1.0% to about 5.0% of isodecyl oleate;
(ab) about 1.0% to about 5.0% of dicaprylyl maleate;
(ac) about 1.0% to about 5.0% of octyldodecyl neopentanoate;
(ad) about 0.1% to about 2.0% of glyceryl stearate;
(ae) about 0.1% to about 2.0% of steareth-2;
(af) about 0.14 to about 3.04 of steareth-21;
(ag) about 0.14 to about 2.04 of $C_{13}$–$C_{14}$ isoparaffin;
(ah) about 0.14 to about 2.04 of PEG-100 stearate;
(ai) about 0.14 to about 2.04 of cetyl alcohol;
(aj) about 0.14 to about 2.04 of laureth-7;
(ak) about 1.04 to about 3.04 of dimethicone;
(al) about 0.14 to about 2.04 of polyacrylamide;
(am) about 0.014 to about 2.04 of carrageenan;
(an) about 0.014 to about 1.04 of xanthan gum;
(ao) about 0.14 to about 3.04 of silica;
(ap) about 0.014 to about 2.0% of glycerin;
(aq) about 0.14 to about 2.04 of butylene glycol;
(ar) about 0.014 to about 2.04 simethicone;
(as) about 0.14 to about 2.04 of PEG-40 hydrogenated castor oil;
(at) about 0.014 to about 2.04 of mineral oil;
(au) about 0.014 to about 1.04 of sodium citrate;
(av) about 0.014 to about 1.04 of trisodium EDTA;
(aw) about 0.014 to about 1.04 of phenoxyethanol;
(ax) about 0.014 to about 1.04 of chlorphenesin;
(ay) about 0.014 to about 1.04 of methylparaben;
(az) about 0.014 to about 1.04 of butylparaben;
(ba) about 0.014 to about 1.04 of propylparaben; and
(bb) about 0.01% to about 1.04 of titanium dioxide;
wherein the propylene glycol, the hydrolyzed wheat protein, the mannitol, the glycogen, the yeast extract, the ginseng extract, the linden extract, the calcium pantothenate, the horse chestnut extract and the biotin comprise an anti-pollution complex, the phospholipids, the panthenol, the Crataegus extract, and the cholesterol comprise a micellar complex, the octyl methoxycinnamate and the oxybenzone comprise an anti-actinic complex, and the melanin, the nocopheryl acetate, the retinyl palmitate, and the ascorbyl palmitate comprise an anti-free radical complex.

62. A cosmetic composition comprising: water, and emulsified and dispersed in the water:
(a) about 0.01% to about 2.0% of propylene glycol;
(b) about 0.01% to about 1.0% of hydrolyzed wheat protein;
(c) about 0.001% to about 1.0% of mannitol;
(d) about 0.001% to about 1.0% of glycogen;
(e) about 0.001% to about 1.0% of yeast extract;
(f) about 0.001% to about 1.0% of ginseng extract;
(g) about 0.001% to about 1.0% of linden extract;
(h) about 0.001% to about 1.0% of calcium pantothenate;
(i) about 0.001% to about 1.0% of horse chestnut extract;

(j) about 0.001% to about 1.0% of biotin;
(k) about 0.001% to about 1.0% of phospholipids;
(l) about 0.001% to about 1.0% of glycosphingolipids;
(m) about 0.01% to about 2.0% of panthenol;
(n) about 0.001% to about 1.0% of Crataegus extract;
(o) about 0.001% to about 1.0% of cholesterol;
(p) about 0.001% to about 1.0% of cholesteryl/behenyl/octyldodecyl lauroyl glutamate;
(q) about 0.001% to about 1.0% of lysine lauroyl methionate;
(r) about 0.001% to about 1.0% of melanin;
(s) about 0.01% to about 2.0% of tocopheryl acetate;
(t) about 0.01% to about 2.0% of retinyl palmitate;
(u) about 0.01% to about 2.0% of ascorbyl palmitate;
(v) about 0.01% to about 2.0% of aloe extract;
(w) about 0.01% to about 2.0% of matricaria extract;
(x) about 0.01% to about 2.0% of horsetail extract;
(y) about 0.1% to about 10.0% of titanium dioxide;
(z) about 2.0% to about 8.0% of neopentyl glycol dioctanoate diisostearate;
(aa) about 2.0% to about 8.0% of octyl palmitate;
(ab) about 1.0% to about 4.0% of cetearyl glucoside;
(ac) about 1.0% to about 3.0% of squalane;
(ad) about 1.0% to about 3.0% of dimethicone;
(ae) about 1.0% to about 8.0% of caprylic/capric triglyceride;
(af) about 0.01% to about 2.0% of mineral oil;
(ag) about 0.01% to about 2.0% of cetyl alcohol;
(ah) about 0.01% to about 2.0% of steareth-2;
(ai) about 0.1% to about 3.0% of steareth-21;
(aj) about 0.1% to about 2.0% of laureth-7;
(ak) about 0.1% to about 2.0% of PEG-40 hydrogenated castor oil;
(al) about 0.1% to about 2.0% of polyacrylamide;
(am) about 0.1% to about 2.0% of butylene glycol;
(an) about 0.01% to about 1.0% of xanthan gum;
(ao) about 0.1% to about 5.0% of hexylene glycol;
(ap) about 0.01% to about 2.0% of fructose;
(aq) about 0.01% to about 2.0% of glucose;
(ar) about 0.01% to about 2.0% of sucrose;
(as) about 0.01% to about 2.0% of urea;
(at) about 0.01% to about 2.0% of dextrin;
(au) about 0.01% to about 2.0% of alanine;
(av) about 0.01% to about 2.0% of glutamic acid;
(aw) about 0.01% to about 2.0% of aspartic acid;
(ax) about 0.01% to about 2.0% of hexyl nicotinate;
(ay) about 0.1% to about 2.0% of $C_{13}$–$C_{14}$ isoparaffin;
(az) about 0.1% to about 2.0% of glycerin;
(ba) about 0.01% to about 1.0% of sodium citrate;
(bb) about 0.01% to about 1.0% of disodium EDTA;
(bc) about 0.01% to about 1.0% of chlorphenesin;
(bd) about 0.01% to about 1.0% of methylparaben;
(be) about 0.01% to about 1.0% of propylparaben;
(bf) about 0.01% to about 1.0% of butylparaben; and
(bg) about 0.01% to about 1.0% of phenoxyethanol;
wherein the propylene glycol, the hydrolyzed wheat protein, the mannitol, the glycogen, the yeast extract, the ginseng extract, the linden extract, the calcium pantothenate, the horse chestnut extract, and the biotin comprise an anti-pollution complex, the phospholipids, the glycosphingolipids, the panthenol, the Crataegus extract, the cholesterol, the cholesteryl/behenyl/octyldodecyl lauroyl glutamate, and the lysine lauroyl methionate comprise a micellar complex, the titanium dioxide comprises a sunscreen, and the melanin, the tocopheryl acetate, the retinyl palmitate, and the ascorbyl palmitate comprise an anti-free radical complex.

* * * * *

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 1, lines 35, 36, 37, delete ", in addition to protection from ultraviolet light, protection from free radical activity, and moisturization of the skin." after the word "pollution"

Column 1, lines 40 & 41, "control of oil" should read --controlling oil--

Column 1, line 57, delete "(4) a sunscreen. after the word "and"

Column 1, line 60, "each is" should read --are each--

Column 1, lines 61 & 62, delete "of at least one environmental stress selected from the group consisting" after the word "effect"

Column 7, lines 44 & 45, delete "of at least one environmental stress selected from the group consisting" after the word "effect"

Column 1, lines 63 & 64, delete "moisture loss and free radical activity" after the word "pollutants"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 7, lines 46 & 47, delete "moisture loss and free radical activity" after the word "pollutants"

Column 1, lines 65, 66 & 67, delete "The sunscreen is present in a quantity sufficient to protect the skin against at least one of UV-A and UV-B solar radiation." after the word "applied."

Column 2, line 7 "the sunscreen" should read --a cosmetic composition according to the present invention preferably further--

Column 2, lines 12 & 13, delete "Alternatively, the sunscreen can comprise titanium dioxide" after the word "methoxycinnamate"

Column 2, line 44, "20" should read --19--

Column 12, line 28, "20" should read --19--

Column 2, line 64, delete "; and (20) simethicone" after the word "triglyceride"

Column 4, line 11 "0.01%" should read --0.1%--

Column 5, line 17 "1.0%" should read --1.01%--

UNITED STATES PATENT AND TRADEMARK OFFICE
CERTIFICATE OF CORRECTION

PATENT NO. : 5,571,503  PAGE 3 of 19

DATED : November 5, 1996

INVENTOR(S) : Mausner

It is certified that error appears in the above-identified patent and that said Letters Patent is hereby corrected as shown below:

Column 5, line 17, "3.0%" should read --5.0%--

Column 5, line 26, delete "(44) about 0.01% to about 1.0% of simethicone;" after the word "glycol;"

Column 5, line 27, "(45)" should read --(44)--

Column 5, line 29, "(46)" should read --(45)--

Column 5, line 30, "(47)" should read --(46)--

Column 5, line 31, "(48)" should read --(47)--

Column 5, line 32, "(49)" should read --(48)--

Column 5, line 33, "(50)" should read --(49)--

Column 5, line 34, "(51)" should read --(50)--

Column 5, line 35, "(52)" should read --(51)--

Column 5, line 36, "(53)" should read --(52)--

Column 5, line 37, "(54)" should read --(53)--

UNITED STATES PATENT AND TRADEMARK OFFICE
CERTIFICATE OF CORRECTION

PATENT NO. : 5,571,503         PAGE 4 of 19

DATED      : November 5, 1996

INVENTOR(S) :   Mausner

It is certified that error appears in the above-identified patent and that said Letters Patent is hereby corrected as shown below:

Column 7, line 20, insert --optionally, an anti-actinic complex; after the numeral "(4)"

Column 7, line 20, delete "a sunscreen" after the numeral "(4)"

Column 8, lines 19-23, delete "One source of the ingredients of the anti-pollution complex is a complex marketed as S.P.C. LS 8425 by Laboratories Seroblologiques S.A., 3, rue de Seichamps, 55420 Pulnoy, France. Other commercially available sources of these ingredients exist." after the word "composition."

Column 9, lines 46-62, delete "3. The Sunscreen

The sunscreen can comprise either titanium dioxide or an anti-actinic complex. If an anti-actinic complex is used, titanium dioxide can optionally be used in addition; in that case, its primary function is that of a pigment. The sunscreen is present in a quantity sufficient to protect the skin against at least one of UV-A and UV-B solar radiation.

When the sunscreen is titanium dioxide, it is typically

UNITED STATES PATENT AND TRADEMARK OFFICE
CERTIFICATE OF CORRECTION

PATENT NO. : 5,571,503         PAGE   5   of   19

DATED       : November 5, 1996

INVENTOR(S) : Mausner

It is certified that error appears in the above-identified patent and that said Letters Patent is hereby corrected as shown below:

present in a concentration of from about 0.1% to about 10.0%.

When the anti-actinic complex is used, it provides a SPF of 15. Preferably, the anti-actinic complex comprises octyl methoxycinnamate and oxybenzone. Preferably, for compositions employing the anti-actinic complex, octyl methoxycinnamate comprises from about 2.0% to about 7.5% of the composition, and oxybenzone comprises from about 2.0% to about 6.0% of the composition." after the word "aggression."

Column 9, line 46, insert --3. <u>The Anti-Actinic Complex</u>

The anti-actinic complex, whose use is optional, provides protection against exposure to the sun. As used, the anti-actinic complex provides a SPF of 15. Preferably, the anti-actinic complex comprises octyl methoxycinnamate and oxybenzone. Preferably, for compositions employing the anti-actinic complex, octyl methoxycinnamate comprises from about 2.0% to about 7.5% of the composition, and oxybenzone comprises from about 2.0% to about 6.0% of the composition.-- after the word "aggression"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 12, line 66, "0.18" should read --0.1%--

Column 13, line 14, "1.0%" should read --1.01%--

Column 13, line 14, "3.0%" should read --5.0%--

Column 13, line 18, "Yet another" should read --Another--

Column 13, lines 41 & 42, delete "Titanium dioxide also provides protection against UV-A and UV-B radiation." after the word "dioxide"

Table II, column 16, line 24, "mannitol" should read --Mannitol--

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Table II, column 16, line 37, "Simethicone" should read --Dimethicone--

Table III, column 16, line 59, "0.1-10.0" should read --0.1-1.00--

Column 18, lines 21-23, delete ", but includes titanium dioxide as a sunscreen to provide protection against UV-A and UV-B radiation" after the word "complex"

Column 18, Lines 27-30, delete ", free radical and ultraviolet light protection, while for the first time, innovatively providing significant protection against several specific pollutants in the environment" after the word "moisturization"

Column 18, lines 27-30, insert --of the skin and control of oil, as well as providing significantly improved protection against environmental pollutants, free radical activity, and sunlight.-- after the word "moisturization"

UNITED STATES PATENT AND TRADEMARK OFFICE
CERTIFICATE OF CORRECTION

PATENT NO. : 5,571,503  PAGE __8__ of __19__

DATED : November 5, 1996

INVENTOR(S) : Mausner

It is certified that error appears in the above-identified patent and that said Letters Patent is hereby corrected as shown below:

Column 18, claim 1, 58-59, delete "and (d) a sunscreen;" after the word "acid;".

Column 18, claim 1, lines 62-63, delete "of at least one environmental stress selected from the group consisting" after the word "effect"

Column 22, claim 48, lines 21-22, delete "of at least one environmental stress selected from the group consisting" after the word "effect"

Column 26, claim 54, lines 9-10, delete "of at least one environmental stress selected from the group consisting" after the word "effect"

Column 27, claim 56, lines 62-63, delete "of at least one environmental stress selected from the group consisting" after the word "effect"

Column 23, claim 50, line 28, delete "of at least one environmental stress selected from the group consisting" after the word "effect"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 24, claim 52, lines 27-28, delete "of at least one environmental stress selected from the group consisting" after the word "effect"

Column 29, claim 58, lines 50-51, delete "of at least one environmental stress selected from the group consisting" after the word "effect"

Column 18, claim 1, lines 64-65, delete "moisture loss, and free radical activity" after the word "pollutants"

Column 23, claim 50, line 30, delete "moisture loss, and free radical activity" after the word "pollutants"

Column 22, claim 48, line 23, delete "moisture loss, and free radical activity" after the word "pollutants"

Column 24, claim 52, line 29, delete "moisture loss, and free radical activity" after the word "pollutants"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 26, claim 54, line 11, delete "moisture loss, and free radical activity" after the word "pollutants"

Column 19, claim 1, lines 1-3, delete ", and the sunscreen being present in a quantity sufficient to protect the skin against at least one of UV-A and UV-B solar radiation" after the word "applied"

Column 22, claim 48, lines 25-27, delete ", and the sunscreen being present in a quantity sufficient to protect the skin against at least one of UV-A and UV-B solar radiation" after the word "applied"

Column 23, claim 50, lines 31-33, delete ", and the sunscreen being present in a quantity sufficient to protect the skin against at least one of UV-A and UV-B solar radiation" after the word "applied"

Column 24, claim 52, lines 30-32, delete ", and the sunscreen being present in a quantity sufficient to protect the skin against at least one of UV-A and UV-B solar radiation" after the word "applied"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 26, claim 54, lines 12-14, delete ", and the sunscreen being present in a quantity sufficient to protect the skin against at least one of UV-A and UV-B solar radiation" after the word "applied"

Column 27, claim 56, lines 65-67, delete ", and the sunscreen being present in a quantity sufficient to protect the skin against at least one of UV-A and UV-B solar radiation" after the word "applied"

Column 29, claim 58, lines 54-56, delete ", and the sunscreen being present in a quantity sufficient to protect the skin against at least one of UV-A and UV-B solar radiation" after the word "applied"

Column 27, claim 56, lines 63-64, delete "moisture loss, and free radical activity" after the word "pollutants"

Column 20, claim 30, line 45, "20" should read --19--

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 19, claim 6, lines 18-19, "wherein the sunscreen comprises" should read --further comprising--

Column 19, claim 6, line 23, insert --, the anti-actinic complex being present in a quantity sufficient to detectably reduce the damaging effect of environmental pollutants on the skin of the wearer to whom the composition is applied-- after the word "thereof"

Column 22, claim 48, lines 6-8, delete "a sunscreen comprising" after the word "panthenol;"

Column 22, claim 48, lines 6, delete "the anti-actinic" after the word "complex"

Column 23, claim 50, lines 13-14, delete "the anti-actinic" after the word "complex"

Column 22, claim 48, line 17, insert --the anti-actinic complex-- after the word "complex" (first occurrence)

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 26, claim 54, line 5, insert --the anti-actinic complex-- after the word "complex", (first ocurrence)

Column 27, claim 56, line 57, insert --the anti-actinic complex-- after the word "complex", (first occurrence)

Column 23, claim 50, line 25, insert --the anti-actinic complex,-- after the word "complex,"(first occurrence)

Column 24, claim 52, lines 23, insert --the anti-actinic complex,-- after the word "complex,"

Column 24, claim 52, line 15, delete "a sunscreen comprising titanium dioxide" after the letter "(c)" insert --an anti-actinic complex comprising octyl methoxycinnamate and oxybenzone-- after the letter "(c)"

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 28, claim 58, line 64, delete "(d)" after the word "dioxide"

Column 25, claim 54, line 30, "a sunscreen comprising an anti-actinic complex, the" should read --an--

Column 27, claim 56, line 10, "a sunscreen comprising an anti-actinic complex, the" should read --an--

Column 25, claim 54, line 32, "octyl methoxycinnamate" should read --octyl methoxycinnamate--

Column 26, claim 56, line 58, "watery" should read --water--

Column 27, claim 56, line 46 delete "(aa) simethicone" after the word "glycol,"

Column 27, claim 56, line 47, "(ab)" should read --(aa)--

Column 27, line 48, "(ac)" should read --(ab)--

UNITED STATES PATENT AND TRADEMARK OFFICE
CERTIFICATE OF CORRECTION

PATENT NO. : 5,571,503

DATED : November 5, 1996

INVENTOR(S) : Mausner

PAGE 15 of 19

It is certified that error appears in the above-identified patent and that said Letters Patent is hereby corrected as shown below:

```
Column 27, line 49, "(ad)" should read --(ac)--

Column 27, line 50, "(ae)" should read --(ad)--

Column 27, line 51 "(af)" should read --(ae)--

Column 27, line 52, "(ag)" should read --(af)--

Column 27, line 53, "(ah)" should read --(ag)--

Column 27, line 54, "(ai)" should read --(ah)--

Column 27, line 55, "(aj)" should read --(ai)--

Column 29, claim 58, line 2, "(e)" should read --(d)--

Column 29, claim 58, line 3, "(f)" should read --(e)--

Column 29, claim 58, line 4, "(g)" should read --(f)--

Column 29, claim 58, line 5, "(h)" should read --(g)--

Column 29, claim 58, line 6, insert --(h) titanium dioxide;--
after the word "extract"
```

UNITED STATES PATENT AND TRADEMARK OFFICE
CERTIFICATE OF CORRECTION

PATENT NO. : 5,571,503  PAGE 16 of 19

DATED : November 5, 1996

INVENTOR(S) : Mausner

It is certified that error appears in the above-identified patent and that said Letters Patent is hereby corrected as shown below:

Column 30, claim 60, line 27, "cosmetic" should read --skin-cream--

Column 32, claim 61, line 14, "0.14" should read --0.1%-- "3.04" should read --3.0%--

Column 32, line 15(ag), "0.14" should read --0.1%--, "2.04" should read --2.0%--

Column 32, line 16(ah), "0.14" should read --0.1%--, "2.04" should read --2.0%--

Column 32, line 17(ai), "0.14" should read --0.1%--, "2.04" should read --2.0%--

Column 32, line 18(aj), "0.14" should read --0.1%--, "2.04%" should read --2.0%--

Column 32, line 19(ak), "1.04" should read --1.01%--, "3.04" should read --5.0%--

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 32, line 20(al), "0.14" should read --0.1%--, "2.04" should read --2.0%--

Column 32, line 21(am), "0.14" should read --0.01%--, "2.04" should read --2.0%--

Column 32, line 22(an), "0.014" should read --0.01%--, "1.04" should read --1.0%--

Column 32, line 23(ao), "0.14" should read --0.1%--, "3.04" should read --3.0%--

Column 32, line 24(ap), "0.014" should read --0.01%--

Column 32, line 25(aq), "0.14" should read --0.1%--, "2.04" should read --2.0%--

Column 32, line 26, claim 61, delete "about 0.014 to about 2.04 simethicone" after the letters "(ar)"

Column 32, line 27(as), delete "(as)" and "0.14" and "2.04" should read --(ar)--0.1% and --2.0%--

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 32, line 29(at), "(at)" should read --(as)--, "0.014" should read --0.01%--, "2.04" should read --2.0%--

Column 32, line 30(au), "(au)" should read --(at)--, "0.014" should read --0.01%--, "1.04" should read --1.0%--

Column 32, line 31(av), "(av)" should read --(au)--, "0.014" should read --0.01%--, "1.04" should read --1.0%--

Column 32, line 32(aw), "(aw)" should read --(av)--, "0.014" should read --0.01%--, "1.04" should read --1.0%--

Column 32, line 33(ax), "(ax)" should read --(aw)--, "0.014" should read --0.01%--, "1.04" should read --1.0%--

Column 32, claim 61, line 34, "(ay)" should read --(ax)--, "0.014" should read --0.01%--, "1.04" should read --1.0%--

Column 32, line 35, "(az)" should read --(ay)--, "0.014" should read --0.01%--, "1.04" should read --1.0%--

Column 32, line 36, "(ba)" should read --(az)--, "0.014" should read --0.01%--, "1.04" should read --1.0%--

UNITED STATES PATENT AND TRADEMARK OFFICE
CERTIFICATE OF CORRECTION

PATENT NO. : 5,571,503

DATED : November 5, 1996

INVENTOR(S) : Mausner

It is certified that error appears in the above-identified patent and that said Letters Patent is hereby corrected as shown below:

Column 32, line 37, "(bb)" should read --(ba)--, "1.04" should read --1.0%--

Column 32, line 46, "nocopheryl" should read --tocopheryl--

Signed and Sealed this

Twenty-first Day of July, 1998

Attest:

BRUCE LEHMAN

Attesting Officer

Commissioner of Patents and Trademarks